US008468872B2

(12) United States Patent
Lee et al.

(10) Patent No.: US 8,468,872 B2
(45) Date of Patent: Jun. 25, 2013

(54) HYDROGEN SENSOR AND METHOD OF MANUFACTURING THE SAME

(75) Inventors: Woo Young Lee, Seoul (KR); Jun Min Lee, Seongnam Si (KR); Eun Yeong Lee, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 352 days.

(21) Appl. No.: 13/059,882

(22) PCT Filed: Dec. 3, 2010

(86) PCT No.: PCT/KR2010/008618
§ 371 (c)(1),
(2), (4) Date: Feb. 18, 2011

(87) PCT Pub. No.: WO2011/081308
PCT Pub. Date: Jul. 7, 2011

(65) Prior Publication Data
US 2011/0259083 A1 Oct. 27, 2011

(30) Foreign Application Priority Data

Dec. 29, 2009 (KR) .......................... 10-2009-132402
Apr. 28, 2010 (KR) ............................ 10-2010-39531
Aug. 23, 2010 (KR) ............................ 10-2010-81180

(51) Int. Cl.
*G01N 27/04* (2006.01)
*G01M 3/04* (2006.01)

(52) U.S. Cl.
USPC ............... 73/23.2; 73/31.03; 73/31.05; 73/40

(58) Field of Classification Search
USPC ......................................................... 977/900
See application file for complete search history.

(56) References Cited

U.S. PATENT DOCUMENTS 7,237,429 B2 * 7/2007 Monty et al. ................... 73/23.2
7,340,941 B1 * 3/2008 Fruhberger et al. .......... 73/24.01

OTHER PUBLICATIONS

F. Dimeo et al., "Micro-Machined Thin Film H2 Gas Sensors", 2003, Annual Merit Review.
Reginald M. Penner et al., "Hydrogen Sensors and Switches from Electrodeposited Palladium Mesowire Arrays", Science , Sep. 2001, pp. 227-2231, vol. 293.

* cited by examiner

*Primary Examiner* — Peter Macchiarolo
*Assistant Examiner* — Irving A Campbell
(74) *Attorney, Agent, or Firm* — Sughrue Mion, PLLC

(57) ABSTRACT

A novel method of manufacturing a hydrogen sensor is disclosed. The method includes the steps of forming a thin film made of a transition metal or an alloy thereof on a surface of an elastic substrate, and forming a plurality of nanogaps in the thin film formed on the surface of the elastic substrate by applying a tensile force to the elastic substrate. The nanogaps are formed as the thin film is stretched in a direction in which the tensile force acts while being contracted in a direction perpendicular to the direction in which the tensile force acts when the tensile force is applied, and is contracted again in the direction in which the tensile force is released while being stretched again in the direction perpendicular to the direction in which the tensile force is released when the tensile force is released.

29 Claims, 19 Drawing Sheets

(a)

(b)

(c)

(a)

(b)

(c)

(d)

HYDROGEN SENSOR AND METHOD OF MANUFACTURING THE SAME

TECHNICAL FIELD

The present invention relates to a hydrogen sensor and a method of manufacturing the same, and more particularly, to a hydrogen sensor, which has a thin film made of a transition metal or an alloy thereof, and a method of manufacturing the same.

BACKGROUND ART

Hydrogen energy has merits in that it is renewable and does not cause environmental pollution, and studies on hydrogen energy are actively underway.

However, there is a problem in that it is difficult for hydrogen gas to be widely applied in daily life unless the safety of use thereof is guaranteed, since hydrogen gas is vulnerable to the danger of explosion if it leaks into the surrounding atmosphere at a concentration of 4% or more. Therefore, along with studies on the utilization of hydrogen energy, the development of a hydrogen gas detection sensor (hereinafter, simply referred to as a "hydrogen sensor"), which can detect the early stages of leakage of hydrogen gas when applied in practice, is actively underway.

The hydrogen sensors that have been developed to date include ceramic/semiconductor sensors (e.g., contact combustion, thermoelectric, and semiconductor thick film sensors), semiconductor device sensors (e.g., Metal-Insulator-Semiconductor Field-Effect Transistor (MISFET) and Metal-Oxide Semiconductor (MOS) sensors), optical sensors, electrochemical sensors (e.g., potentiometric/amperometric sensors), etc.

In the case of the ceramic/semiconductor sensors, many of the ceramic/semiconductor sensors take advantage of the change of electrical conductivity that occurs when gas contacts the surface of the ceramic semiconductor. Since most of the sensors are generally used by being heated in the air, metal oxides (e.g., ceramics, $SnO_2$, $ZnO$, and $Fe_2O_3$), which are stable at high temperatures, are mainly used. However, as a disadvantage, these sensors cannot detect high concentrations of hydrogen gas, since they become saturated in high concentrations of hydrogen gas.

Among these examples, the contact combustion sensor is a type of sensor that detects a change in the combustion heat generated from an oxidation reaction, which occurs through the contact of combustible gas with the surface of the sensor. This sensor has advantages in that its output is proportional to the concentration of gas, the precision of detection is high, and it is rarely influenced by ambient temperatures or humidities. However, this sensor has disadvantages in that its operating temperature has to be high and it is not selective.

In addition, in the semiconductor device sensors (e.g., MISFET and MOS sensors) and the optical sensors, which use a gasochromic material, the light transmissivity of which varies depending on the adsorption of hydrogen, palladium (Pd), which exhibits good ability to absorb hydrogen gas, is used. However, these sensors have a disadvantage in that their performance degrades when they are repeatedly exposed to high concentrations of hydrogen gas.

Finally, the electrochemical sensors are devices that electrochemically oxidize or reduce the gas that is to be detected, and measure current flowing through an external circuit at that time. These sensors can be divided into an electrostatic type, a galvanic cell type, an ion cell type, and the like depending on the principle of detection. Although these sensors have various gas detection abilities, they suffer from the disadvantage whereby the method of manufacturing the sensors is complicated and difficult.

Materials for sensors that have been recently used as hydrogen detection technologies include a Pd thin film sensor, a semiconductor sensor, which uses an MISFET or the like, a carbon nanotube sensor, a titania nanotube sensor, and the like (F. Dimeo et al., 2003 *Annual Merit Review*). However, despite the respective advantages of these technologies, the performance of these sensors is still dissatisfactory in terms of initial concentration of hydrogen that can be detected, response time, detection temperature, drive voltage, and the like, which can be regarded as key factors of a hydrogen sensor.

One technology that was recently developed discloses the use of the phenomenon whereby, when sites on which Pd particles can be generated are prepared using a graphite layer through the reaction between Pd and hydrogen, the resultant Pd particles are formed into a wire, in which Pd lattices are expanded and connected to each other as hydrogen is introduced into a functionalized substrate, thereby reducing electrical resistance (Penner et al. *Science* 293 (2001), 2227-2231). Here, the lattice expansion of Pd in response to hydrogen adsorption was experimentally observed, and an electrical signal was thereby detected by arraying the Pd nanoparticles in the form of a discontinuous wire. However, the disadvantages are that the method of manufacturing the sensor is complicated and the minimum concentration that can be detected is high.

In general, the hydrogen gas detection sensors using the Pd thin film are widely used, since they exhibit hydrogen detection performance that is far better than those of sensors manufactured using other materials. In such hydrogen sensors of the related art, a method of expanding lattices by bringing the Pd particles into close contact with the substrate by applying a strong force to the Pd particles via sputtering, vapor deposition, or the like was used. However, the sensitivity to hydrogen was not high, since the amount of expansion was reduced by the force of bonding to the substrate. In addition, in the case in which the Pd particles are not bonded to the substrate, if the exposure to hydrogen is stopped after the Pd lattices are expanded upon exposure to hydrogen, the initial state was not restored due to the bonding force between the Pd particles, thereby entailing the disadvantage of low reproducibility. Furthermore, the hydrogen sensors using Pd particles have other problems in that they react only to a high concentration of hydrogen and their initial resistance value changes when they are no longer exposed to hydrogen.

Although the hydrogen sensors of the related art have overcome some of the problems with the existing hydrogen sensors as described above, they fail as replacements for the existing sensors for reasons pertaining to detection ability, sensitivity, stability, high speed of response at low concentrations, and the like.

Therefore, studies on materials and structures that can optimize hydrogen detection performance are underway, and attempts to improve hydrogen detection performance using nanomaterials are continually being made.

Pd, as a representative nanomaterial, has a property such that it reacts with hydrogen regardless of the surrounding environment, and exhibits a phenomenon in which its lattice constant increases when it chemically absorbs hydrogen gas, thereby showing increased resistance when current is induced.

Based on this phenomenon, recent studies on solid hydrogen sensors that react only to hydrogen using Pd nanowires (NWs), the surface area of which is maximized, are actively underway. The hydrogen sensor using the Pd NWs is adapted to detect hydrogen based on the phenomenon by which the resistance of the Pd NWs changes depending on whether or not hydrogen is present.

Methods of manufacturing the Pd NWs that have been developed to date include a method using a Highly Oriented Pyrolytic Graphite (HOPG) template, a method using E-Beam lithography (EBL), a method using Dielectrophoresis (DEP), and the like.

The method of using an HOPG template is a method of electrochemically producing Pd NWs in a nanotemplate of a substrate. However, this method has disadvantages in that the manufacturing process is complicated and time-consuming and the production yield is low. The low production yield is attributable to the resultant Pd NWs, which are difficult to impart with a constant resistance value due to errors during the manufacturing process.

In addition, the method using EBL is a method of electrochemically forming Pd NWs after forming a nanopattern on a substrate. However, this method has the disadvantages of low production yield and high manufacturing cost.

The method using DEP is a method of producing NWs by forming a layer of a NW material on a substrate, followed by supplying a high-frequency AC power source through metal electrodes. However, this method also has disadvantages in that the manufacturing process is complicated and the production yield is low, since it is impossible to produce Pd NWs having a uniform shape.

Therefore, the development of a novel manufacturing process, which can manufacture a Pd hydrogen sensor at a low cost and in a simple process while ensuring that the hydrogen detection performance of Pd is maintained unchanged, is required.

DISCLOSURE

Technical Problem

The present invention has been devised in order to solve the foregoing problems with the related art, and it is therefore an object of the invention to provide a novel method of manufacturing a hydrogen sensor, which saves time and is inexpensive, to replace a method of manufacturing a hydrogen sensor of the related art, which is complicated and time-consuming and has a low production yield, and a hydrogen sensor manufactured thereby.

It is another object of the invention to provide a hydrogen sensor, which has a very low price and exhibits high performance, and a method of manufacturing the same, in which the reaction reproducibility of the hydrogen sensor to hydrogen is improved such that the hydrogen sensor can precisely detect hydrogen.

Technical Solution

In order to realize the foregoing object, the present invention provides a novel method of manufacturing a hydrogen sensor. The method includes the following steps of: forming a thin film made of a transition metal or an alloy thereof on a surface of an elastic substrate, and forming a plurality of nanogaps in the thin film formed on the surface of the elastic substrate by applying a tensile force to the elastic substrate. The nanogaps are formed as the thin film is stretched in a direction in which the tensile force acts while being contracted in a direction perpendicular to the direction in which the tensile force acts when the tensile force is applied, and is contracted again in the direction in which the tensile force is released while being stretched again in the direction perpendicular to the direction in which the tensile force is released when the tensile force is released.

In an embodiment, the transition metal may be selected from among Pd, Pt, Ni, Ag, Ti, Fe, Zn, Co, Mn, Au, W, In, and Al.

In an embodiment, the alloy may be selected from among Pd—Ni, Pt—Pd, Pd—Ag, Pd—Ti, Pd—Fe, Pd—Zn, Pd—Co, Pd—Mn, Pd—Au, Pd—W, Pt—Ni, Pt—Ag, Pt—Ti, Fe—Pt, Pt—Zn, Pt—Co, Pt—Mn, Pt—Au, and Pt—W.

In an embodiment, the transition metal may be Pd, and the alloy may be a Pd alloy.

In an embodiment, the thin film formed on the surface of the elastic substrate may be made of a $Pd_xNi_{1-x}$ alloy that satisfies the relationship: $0.85 \leq x \leq 0.96$.

In an embodiment, the thin film formed on the surface of the elastic substrate may be made of a $Pd_xNi_{1-x}$ alloy that satisfies the relationship: $0.90 \leq x \leq 0.94$.

In an embodiment, the elastic substrate may be a substrate that has a Poisson's ratio ranging from 0.2 to 0.8.

In an embodiment, the tensile force may be applied so that the elastic substrate is stretched 1.05 to 1.50 times.

In an embodiment, the elastic substrate may be made of natural rubber, synthetic rubber, or polymer.

In an embodiment, the tensile force may be applied repeatedly one or more times to the elastic substrate.

In an embodiment, the tensile force may be applied to the elastic substrate in one or more directions.

In an embodiment, the tensile force may be applied repeatedly in a first direction, a second direction perpendicular to the first direction, and a third direction different from the first and second directions.

In an embodiment, the thin film may have a thickness ranging from 1 nm to 100 μm.

In an embodiment, the nanogaps may be formed with a spacing ranging from 1 nm to 10 μm.

In an embodiment, the method may also include the step of heat treating the thin film made of a transition metal or an alloy thereof in which the nanogaps are formed.

In an embodiment, the method may also include the step of performing ion milling on the thin film made of a transition metal or an alloy thereof in which the nanogaps are formed.

According to another aspect of the invention, provided is a novel method of manufacturing a hydrogen sensor. The method includes the following steps of: preparing an elastic substrate; forming a thin film made of Pd or a Pd alloy on the elastic substrate, the Pd or Pd alloy having α phase; forming nanogaps in the thin film in response to volume expansion by changing the α phase of the thin film into β phase by exposing the thin film to hydrogen-containing gas having a predetermined concentration of hydrogen; and changing the β phase of the thin film into the α phase again by stopping the exposure of the thin film to the hydrogen-containing gas.

In an embodiment, the method may also include the step of heat treating the thin film, in which the β is changed into the α phase.

In an embodiment, the method may also include the step of performing ion milling on the thin film, in which the β is changed into the α phase.

In an embodiment, when exposing the thin film to hydrogen-containing gas having a predetermined concentration, the concentration of hydrogen may range from 2% to 15%.

In an embodiment, the thickness of the thin film may be in the range, approximately, from 1 nm to 100 μm.

According to a further aspect of the invention, provided is a hydrogen sensor, which includes a substrate made of an elastic material; a thin film formed on the surface of the substrate, the thin film being made of a transition metal or an alloy thereof; and electrodes formed at opposite ends of the thin film. The thin film has a plurality of nanogaps formed therein by a tensile force that is applied to the substrate.

According to another aspect of the invention, provided is a hydrogen sensor, which includes a substrate made of an elastic material; a thin film formed on the surface of the substrate, the thin film being made of Pd or a Pd alloy and having a plurality of nanogaps formed therein; and electrodes formed at opposite ends of the thin film, wherein the nanogaps are formed via the method of using the phase change.

Advantageous Effects

Unlike the methods of manufacturing hydrogen sensors of the related art (e.g., a semiconductor type, a contact combustion type, a FET type, an electrolyte (electrochemical) type, an optical fiber type, a piezoelectric type, a thermoelectric type, and the like), which involve complicated processes, or commercially-distributed hydrogen sensors (e.g., a contact combustion type hydrogen sensor, a hydrogen sensor bonded with a Pd alloy via a hot plate, a solid Pd/Ag alloy hydrogen sensor, a Pd gate FET hydrogen sensor, and the like), which are bulky, expensive, and inconvenient, the method of manufacturing a hydrogen sensor of the present invention enables the mass-production of a high-performance hydrogen sensor in a short time and at low cost, since it can shape the thin film, which is made of a transition metal (e.g., Pd) or an alloy thereof (e.g., a Pd—Ni alloy), in such a fashion that the thin film has nanogaps, which can detect hydrogen gas, by applying a physical tensile force to the substrate on which the thin film is disposed.

Unlike the methods of manufacturing hydrogen sensors of the related art, which involve complicated processes, the method of manufacturing a hydrogen sensor of the present invention can dispose the thin film made of a transition metal or an alloy thereof on the elastic substrate and stretch the elastic substrate such that the thin film disposed on the substrate is stretched in the direction in which the tensile force acts and is simultaneously compressed in the direction perpendicular thereto. It is possible to easily produce the thin film made of a transition metal or an alloy thereof such that it has nanogaps therein by applying physical strain by a simple method of applying the tensile force to the elastic substrate. Therefore, it is possible to mass-produce an inexpensive high-performance hydrogen sensor, the resistance value of which changes in response to changes in the concentration of hydrogen, thereby remarkably increasing the production yield of the hydrogen sensor.

In addition, unlike the hydrogen sensor of the related art, which is realized on a substrate made of a nonelastic material, such as a silicon oxide substrate, a sapphire substrate, or a glass substrate, the hydrogen sensor of the present invention is produced by disposing the thin film made of a transition metal or an alloy thereof on the surface of the substrate made of an elastic material. Since the hydrogen sensor has its own elasticity, it can be freely installed in various spaces in which the leakage of hydrogen is suspected, thereby widening the range of application thereof. Furthermore, according to the present invention, a high-performance hydrogen sensor can be manufactured in a short time and at low cost, since the nanogaps can be formed through the phase change of the Pd thin film.

BEST MODE

Figure 1:
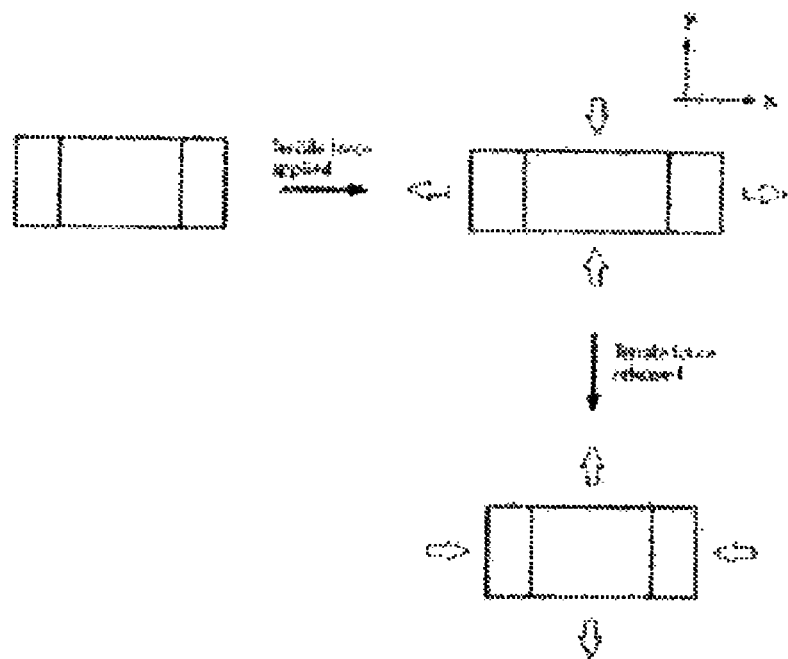
FIG. 1 illustrates an aspect in which an elastic substrate and a thin film disposed on the elastic substrate, the thin film being made of a transition metal or an alloy thereof, are deformed when a tensile force is applied to the elastic substrate on which the thin film made of Pd is disposed.

The present invention will now be described more fully hereinafter with reference to the accompanying drawings, in which exemplary embodiments thereof are shown.

As replacements for he complicated method of the related art, which produces palladium (Pd) nanowires (NWs) using a MicroElectroMechanjcal Systems (MEMS) process, such as lithography, the method. of manufacturing a hydrogen sensor of the present invention can be used to mass-produce a hydrogen sensor having nanogaps therein by disposing a thin film made of a transition metal or an alloy thereof on an elastic substrate and stretching the elastic substrate in a specific direction.

The thin film disposed on the substrate is stretched in the direction in which the tensile force acts while being contracted in the direction perpendicular thereto. In addition, when the tensile force applied to the elastic force is released, the thin film contracts in the direction in which the elastic force is released while being stretched again in the direction perpendicular thereto.

In this fashion, according to the method of manufacturing a hydrogen sensor of the present invention, it is possible to apply physical strain to the thin film made of a transition metal, such as Pd, or an alloy thereof in a simple method of applying a tensile force to the elastic substrate, thereby easily manufacturing a hydrogen sensor having nanogaps therein in a short time and at low cost. Alternatively, it is possible to manufacture a hydrogen sensor having nanogaps therein using the phase change of Pd.

When the nanogaps are formed in the thin film made of a transition metal or an alloy thereof, as described above, resistance is high, since the nanogaps prevent electric current from easily flowing. However, in a hydrogen atmosphere, the lattice constant of the transition metal or the alloy thereof increases since surrounding hydrogen is absorbed, and the nanogaps are filled in response to volume expansion. Thus, the flow of electric current becomes easier, and the resistance decreases. Accordingly, it is possible to measure the concentration of hydrogen by measuring changes in the resistance value that occur in response to the presence or absence of hydrogen gas.

Hereinafter, several embodiments the present invention will now be described greater detail with reference to the accompanying drawings.

1. Embodiment A

First, in order to manufacture a hydrogen sensor of the invention, a thin film made of a transition metal or an alloy thereof is disposed on an elastic substrate.

Here, the substrate performs as a base on which the thin film, which serves as a detector to detect hydrogen, is disposed. The substrate also serves to transmit strain to the thin film disposed on the substrate when a tensile force is applied in the process of manufacturing the hydrogen sensor.

The substrate is made of an elastic material such that it can be stretched in the direction in which the tensile force is applied and can return to its original shape when the tensile force is removed.

Referring to FIG. 1, as is often seen with an elastic material, when the elastic material is stretched in the longitudinal direction (x direction), it is expected that the elastic material will contract in the lateral direction (y direction) as it is stretched in the longitudinal direction, if there are no other conditions except a component of tensile strain in the longitudinal direction. In addition, the tensile strain in the lateral direction (y direction) causes contraction while maintaining a predetermined ratio with respect to the longitudinal tensile strain. Also, when the tensile force applied to the stretched elastic material is released, or the elastic material is compressed in the short axis direction, tensile strain occurs in the lateral direction. Here, the elastic material is deformed while maintaining a constant ratio between the lateral tensile strain and longitudinal shrinkage, the ratio being the same as for the stretching. The value having a predetermined ratio between the lateral tensile strain and longitudinal shrinkage is taken as the Poisson's ratio of elastic material.

As shown in FIG. 1, when the tensile force is applied to the elastic material, the thin film made of Pd or an alloy thereof (hereinafter, also referred to as the "Pd or Pd-alloy thin film"), which is integrally bonded to the surface of the elastic material, is integrally deformed in response to the deformation of the elastic material. Referring to the aspect of the deformation, the thin film is stretched in the x direction while contracting in the y direction when the tensile force is applied, and contracts in the x direction while being stretched in the y direction when the tensile force is released.

Figure 2:
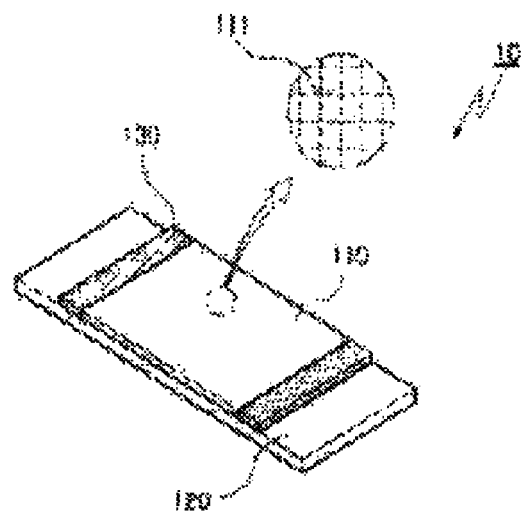
FIG. 2 is a perspective view showing a hydrogen sensor according to an embodiment of the invention.
Figure 3:
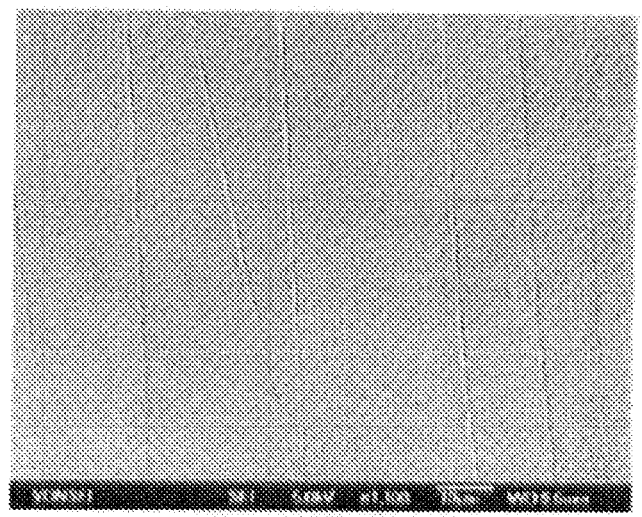
FIG. 3 is pictures showing a Pd thin film having nanogaps formed therein, in which (a) is a microscopic picture at a magnification of about 1000 times, (b) is a microscopic picture at a magnification of about 50 times, and (c) is a three-dimensional (3D) picture.
Figure 3:
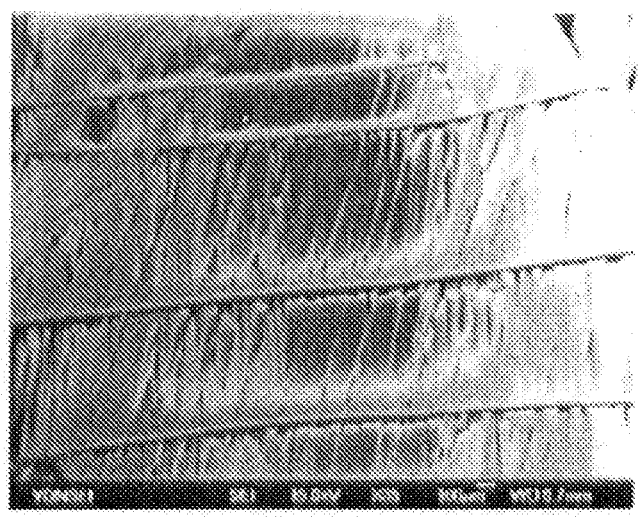
Figure 3:
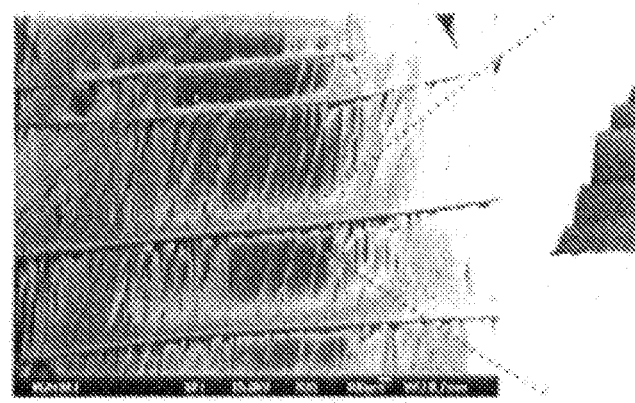

Referring to FIG. 2, which shows the hydrogen sensor according to an embodiment of the invention, it is possible to apply physical strain to the thin film 110, which is integrally bonded to the surface of the elastic substrate 120, by a simple method of applying a tensile force to the elastic substrate. In the Pd or Pd-alloy thin film 110, to which the physical strain is applied, nanogaps 11 are formed, as shown in FIG. 3.

Since the tensile force acting on the elastic substrate 120 is directly transmitted to the Pd or Pd-alloy thin film, the ratios of the stretching and the contraction of the thin film 110 in the stretching direction (x direction) or in the contraction direction (y direction) are determined by the Poisson's ratio of the elastic substrate 120.

In a method of manufacturing the hydrogen sensor 10 according to an embodiment of the invention, the thin film is stretched in the x direction, in which the tensile force acts, while being contracted in the y direction, which is perpendicular to the direction in which the tensile force acts. Therefore, it is necessary to adjust the size of the tensile force acting on the elastic substrate 120 in consideration of the physical strain acting on the thin film 110 and the efficient formation of the nanogaps 11, which are caused by the strain. For these reasons, the elastic substrate 120 has a Poisson's ratio that ranges, preferably, from 0.2 to 0.8, more preferably, from 0.3 to 0.7, and is most preferably 0.5.

In addition, it is preferred that the tensile force acting on the elastic substrate 120 be applied to stretch the elastic substrate 120 such that the nanogaps 11 are uniformly formed in the thin film 110. Here, the characteristics of the elastic substrate 120, as well as the thickness, quality, and other properties of the thin film 110 made of a transition metal or an alloy thereof, which is integrally formed on the surface of the elastic substrate 120, are collectively considered. It is also preferred that the elastic substrate 120 be stretched 1.05 to 1.50 times.

The thin film 110 made of a transition metal or an alloy thereof is disposed on the substrate 120. Here, the present invention is not limited as to the type of transition metal, and various types of transition metal and alloys thereof, which can be expanded by hydrogen, can be used.

Preferably, the transition metal can be selected from among Pd, Pt, Ni, Ag, Ti, Fe, Zn, Co, Mn, Au, W, In, and Al, which can be expanded by hydrogen.

In addition, the alloy can be selected from among Pd'Ni, Pt—Pd, Pd—Ag, Pd—Ti, Pd—Fe, Pd—Zn, Pd—Co, Pd—Mn, Pd—Au, Pd—W, Pt—Ni, Pt—Ag, Pt—Ti, Fe—Pt, Pt—Zn, Pt—Co, Pt—Mn, Pt—Au, and Pt—W, which can be expanded by hydrogen. For example, a Pd—Ni or Pd—Au alloy serves to enhance the durability of a hydrogen sensor, which is made of the Pd—Ni or Pd—Au alloy, and reduce the time necessary for the reaction with hydrogen, since Pd acts as a catalyst in the reaction with hydrogen, and Ni or Au reduces the lattice constant of Pd. It is more preferable that the above transition metal and alloys thereof be Pd and Pd alloys.

In the meantime, the method of disposing the thin film 110 made of a transition metal or an alloy thereof can employ a method that is well known in the art. For example, a physical deposition method, such as sputtering or evaporation, and other deposition methods, such as Chemical Vapor Deposition (CVD) or Atomic Layer Deposition (ALD), can be used.

The elastic substrate 120 can be made of any material as long as it can be stretched in the direction in which a tensile force is applied and can restore its original shape when the tensile force is removed, and examples thereof may include natural rubber, synthetic rubber, or polymer.

Examples of the synthetic rubber may include butadiene-based rubber, isoprene-based rubber, chloroprene-based rubber, nitrile-based rubber, polyurethane-based rubber, silicone-based rubber, and the like. Polydimethylsiloxane (PDMS) can be preferably used, since it has low interfacial free energy, with which a transition metal or an alloy thereof disposed on the substrate can be easily shaped and machined, and has good durability. In addition to PDMS, it is possible to use polyimide-based polymer materials, polyurethane-based polymer materials, fluorocarbon-based polymer materials, acrylic-based polymer materials, polyaniline-based polymer materials, polyester-based polymer materials, and the like by suitably adjusting elasticity as long as they can transmit a tensile force to the thin film made of a transition metal or an alloy thereof.

When a tensile force is applied to the elastic substrate 120 on which the thin film 110 made of a transition metal or an alloy thereof is disposed, as described above, the thin film 110 suffers physical strain, since it is stretched in the x direction, in which the tensile force is applied, and is simultaneously contracted in the y direction, thereby forming the nanogaps 11. Here, the nanogaps 11 can be formed in the thin film even if the tensile force is applied only one time. However, in consideration of the directivity and uniformity with which the nanogaps 11 are formed, it is preferred that the tensile force acting on the elastic substrate 120 be applied repeatedly one or more times.

Figure 4:
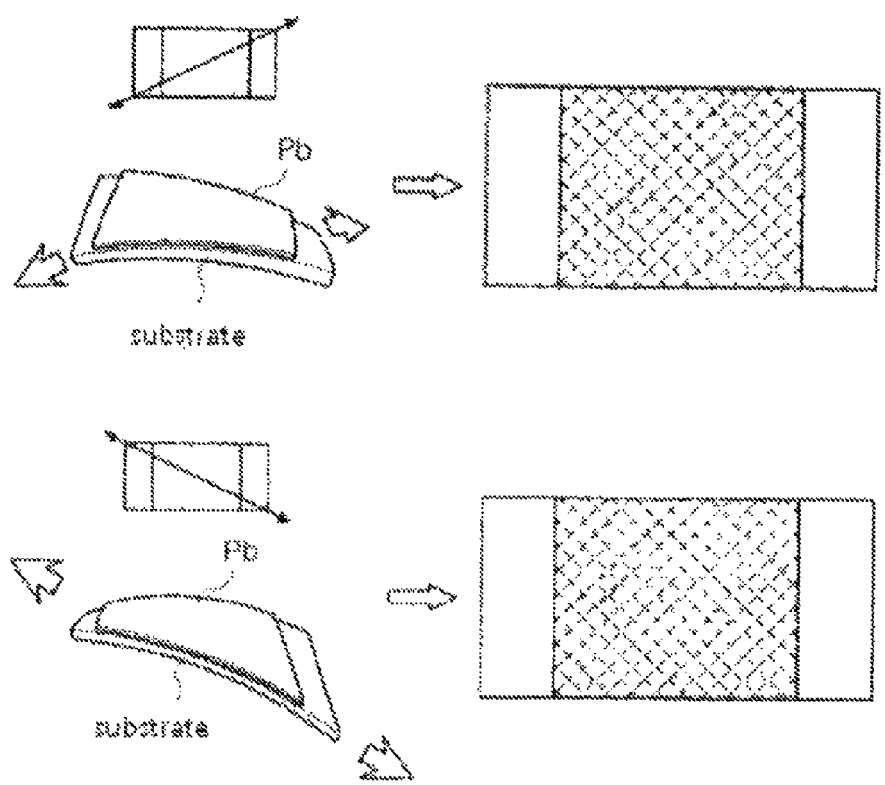
FIG. 4 illustrates a change in the shape of the substrate on which the Pd thin film is disposed, the change in the shape occurring when a tensile force is applied and is then removed in at least one direction.

In addition, although the tensile force can be applied simply in one specific direction, this is not intended to be limiting. In an example, as shown in FIG. 4, if a metal component, which is added to the manufacturing of a Pd alloy, increases the ductility of the alloy, it is possible to promote the formation of the nanogaps in the thin film by applying the tensile force in one or more directions, for example, two or three directions.

When the tensile force is applied in three directions, it is possible to effectively concentrate the strain that acts on the thin film by repeating the application of the tensile force in a first direction, a second direction perpendicular to the first direction, and a third direction different from the first and second directions, and through this processing, to form the nanogaps in the thin film of a transition metal or an alloy thereof. Here, it is possible to effectively concentrate the stain acting on the thin film if the second direction, in which the tensile force is applied, has an angle of 90° with respect to the first direction, and the third direction, in which the tensile force is applied, has an angle greater than ±0° and smaller than ±90° with respect to the first and second directions.

In the meantime, it is preferred that the thickness of the thin film made of a transition metal or an alloy thereof be in the range from 1 nm to 100 μm. The thickness of the thin film made of a transition metal or an alloy thereof relates to whether or not the nanogaps are effectively formed in the thin film when the tensile force is applied to and removed from the substrate. The thinner the film is, the higher the number of nanogaps that can be formed is. However, if the thickness is excessively low, the thin film made of a transition metal or an alloy thereof may be physically damaged and torn when the tensile force is repeatedly applied to the substrate. Therefore, it is preferred that the thickness of the thin film be set in the range from 1 nm to 100 μm such that the thin film can withstand the tensile force applied thereto. In collective consideration of the elastic characteristics of the elastic substrate, the physical properties of the thin film made of a transition metal or an alloy thereof, and the like, the thickness of the thin film can be set, more preferably, in the range from 3 nm to 100 nm, and most preferably, in the range from 5 nm to 15 nm.

In addition, although the substrate is not limited as to the size thereof, it is preferred that the substrate have a width ranging from 0.1 cm to 10 cm, a length ranging from 0.1 cm to 20 cm, and a thickness ranging from 0.01 cm to 1 cm from a practical point of view in collective consideration of both the ease with which the tensile force is applied to the substrate and the size of the hydrogen sensor that is to be manufactured.

Figure 5:
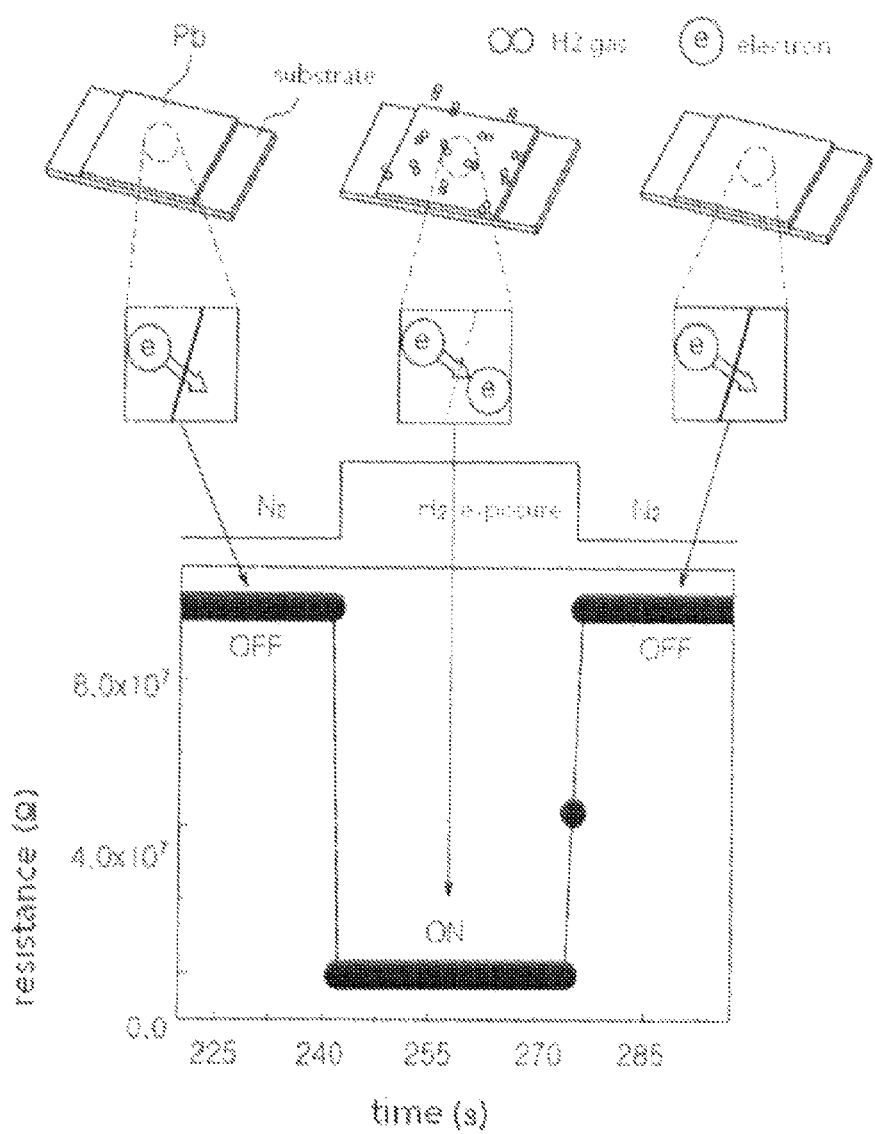
FIG. 5 is an explanatory view showing a change in the resistance value of the hydrogen sensor according to an embodiment of the invention, depending on the presence and absence of hydrogen.

Referring to FIG. 5, the thin film made of a transition metal or an alloy thereof in which the nanogaps are formed using the above-described method exhibits high resistance if no hydrogen is present, since electric current does not smoothly flow due to the nanogaps. However, in a hydrogen atmosphere, the thin film undergoes volume expansion by absorbing hydrogen, and the nanogaps are filled through the volume expansion, thereby lowering the resistance. Therefore, it is possible to use the thin film, in which the nanogaps are formed, as a hydrogen detector in order to detect the concentration of hydrogen by measuring changes in the resistance value.

The width of the nanogaps can be freely adjusted depending on the magnitude and direction of the tensile force, which is applied to the substrate. In consideration of the fact that the nanogaps are filled in response to the expansion of the transition metal or the alloy thereof through the absorption of hydrogen in the hydrogen atmosphere, as well as of the limit to which hydrogen can be detected through changes in the resistance value, it is preferred that the width of the nanogaps range from 1 nm to 10 μm.

In addition, the surface area of the above-noted thin film having the nanogaps can be maximized through ion milling. Methods of performing ion milling on the thin film having the nanogaps include a method of performing ion milling on the upper portion of the substrate having the thin film, and more preferably, a method of applying a resin layer on the substrate having the thin film, forming a resin layer pattern such that only the thin film portion having the nanogaps is exposed, performing ion milling on the exposed thin film portion, and removing the resin layer.

The mechanical properties of the thin film made of a transition metal or an alloy thereof, with the nanogaps formed therein, can be enhanced through heat treatment. Such heat treatment methods include a method of performing heat treatment on the substrate having the thin film in a furnace.

Electrodes are formed on the thin film having the multiple nanogaps therein by depositing a conductive metal on opposite ends of the thin film in the direction parallel to the direction in which the nanogaps are formed, such that current can be induced to the thin film. Here, the thin film having the nanogaps therein is electrically connected to the electrodes. The electrodes formed as described above make it possible to measure changes in the resistance that occur in response to changes in the concentration of hydrogen using a quasi-two probe method. Specifically, the quasi-two probe method induces the current (I+) to one electrode while measuring the voltage from the same electrode, and measures the current (I−) and voltage (V−) output from the other electrode.

The hydrogen sensor produced as above by forming the nanogaps by applying a tensile force to the elastic substrate on which the thin film made of a transition metal or an alloy thereof is disposed, and then forming the electrodes by depositing a conductive metal on the thin film, has a characteristic in that the resistance changes depending on the presence or absence of hydrogen gas, and can be used to measure the concentrations of hydrogen based on this characteristic.

As shown in FIG. 2, the hydrogen sensor according to an embodiment of the invention includes a substrate 120 made of an elastic material, a thin film 110 made of a transition metal or an alloy thereof, the thin film 110 being disposed on the surface of the substrate 120 and having a plurality of nanogaps 110 therein formed by a tensile force applied to the substrate 120, and electrodes 130 formed on opposite ends of the thin film.

Returning to FIG. 5, when the hydrogen sensor 10 is exposed to hydrogen gas, the $H_2$ partial pressure surrounding the Pd thin film having nanogaps becomes higher than that inside the Pd thin film, and hydrogen molecules are dissociated into H atoms through adsorption onto the surface of the Pd thin film in order to lower the interfacial energy of the surface of the Pd thin film. The difference between the $H_2$ partial pressures outside and inside the Pd thin film acts as a driving force with which the H atoms diffuse into the Pd thin film. The H atoms that have diffused into the thin film penetrate into interstitial sites in the lattice (i.e. Face-Centered Cubic (FCC)) structure defined by α-phase Pd atoms, thereby forming PdHx. Here, the H atoms that have occupied the interstitial sites cause an increase in lattice constant.

Therefore, when the lattice constant increases in the hydrogen atmosphere, and thus the volume increases, the nanogaps 11 are filled in response to the increase in the volume, so that the hydrogen sensor 10 has a low resistance. Thus, the thin film having the nanogaps therein can be used as a hydrogen detector in order to detect the concentrations of hydrogen by measuring such changes in the resistance value.

Unlike the existing hydrogen sensors, the hydrogen sensor, which is manufactured using the above-described method, can measure concentrations at room temperature and has a small size, thereby reducing power consumption.

Therefore, the hydrogen sensor of the invention can realize factors that are required for sensors, such as reduced response time and stable operation, while satisfying other characteristics such as low price, small size, low power consumption, and operation at room temperature.

Below, more detailed descriptions will be given of several specific experimental examples of this embodiment.

MANUFACTURING EXAMPLE 1

Pd was deposited, via sputtering, on a PDMS substrate 120 having a width of 20 mm, a length of 10 mm, and a thickness of 0.75 mm. Here, a Pd thin film 110 having a thickness of 7.5 nm, a width of 15 mm, and a length of 10 mm was disposed on the substrate 120.

Afterwards, the substrate 120 was stretched by applying a tensile force five times to the substrate 120 so that the width became 25 mm, and then the tensile force was removed.

As shown in FIG. 3, nanogaps were formed in the Pd thin film 110 by applying the tensile force in the same fashion described above.

The thin film 110 having therein the nanogaps 11 formed through the process described above was subjected to sputtering so that Au electrodes were deposited on opposite ends of the thin film. Thereby, a hydrogen sensor 10 having the thin film 110 and the electrodes 130, which are formed on the PDMS substrate 120 and are electrically connected to each other, was manufactured.

MANUFACTURING EXAMPLE 2

A hydrogen sensor 10 was manufactured in the same method as in Manufacturing Example 1, except that a Pd thin film 110 was formed to a thickness of 10 nm on an elastic substrate 120.

MANUFACTURING EXAMPLE 3

A hydrogen sensor 10 was manufactured in the same method as in Manufacturing Example 1, except that a Pd thin film 110 was formed to a thickness of 12 nm on an elastic substrate 120.

MANUFACTURING EXAMPLE 4

Pd was deposited, via sputtering, on a PDMS substrate 120 having a width of 20 mm, a length of 10 mm, and a thickness of 0.75 mm. Here, the Pd thin film 110 having a thickness of 6 nm, a width of 15 mm, and a length of 10 mm was disposed on the substrate 120.

Afterwards, the substrate 120 was stretched by applying a tensile force to the substrate 120 in the width (first length) so that the width became 25 mm, and then the tensile force was removed such that the substrate returns to its original size.

The substrate 120 to which the tensile force was applied in the first direction was subjected to a tensile force in the diagonal direction (second direction), which extends from the upper right to the lower left, so that the substrate 120 was stretched up to 1.25 times its original diagonal length, and then the substrate was returned to its original size.

Subsequently, after the tensile force was applied in the second direction, the substrate 120 was subjected to a tensile force in the diagonal direction (third direction), which extends from the upper left to the lower right, so that the substrate 120 was stretched up to 1.25 times its original diagonal length, and then the substrate was returned to its original size.

By repeatedly applying the tensile force five times in the first, second, and third directions, nanogaps 11 were formed in the thin film 110, which was disposed on the surface of the substrate 120.

The thin film 110 having the nanogaps 11 formed through the process described above was subjected to sputtering so that Au electrodes were deposited on opposite ends of the thin film. Thereby, a hydrogen sensor 10 having the thin film 110 and the electrodes 130, which are formed on the PDMS substrate 120 and are electrically connected to each other, was manufactured.

EXPERIMENTAL EXAMPLE 1

In order to evaluate the characteristics of hydrogen sensors, which are manufactured according to the manufacturing examples, a measuring system 20, which can perform measurement using a quasi-two probe method, was manufactured and used.

Figure 6:
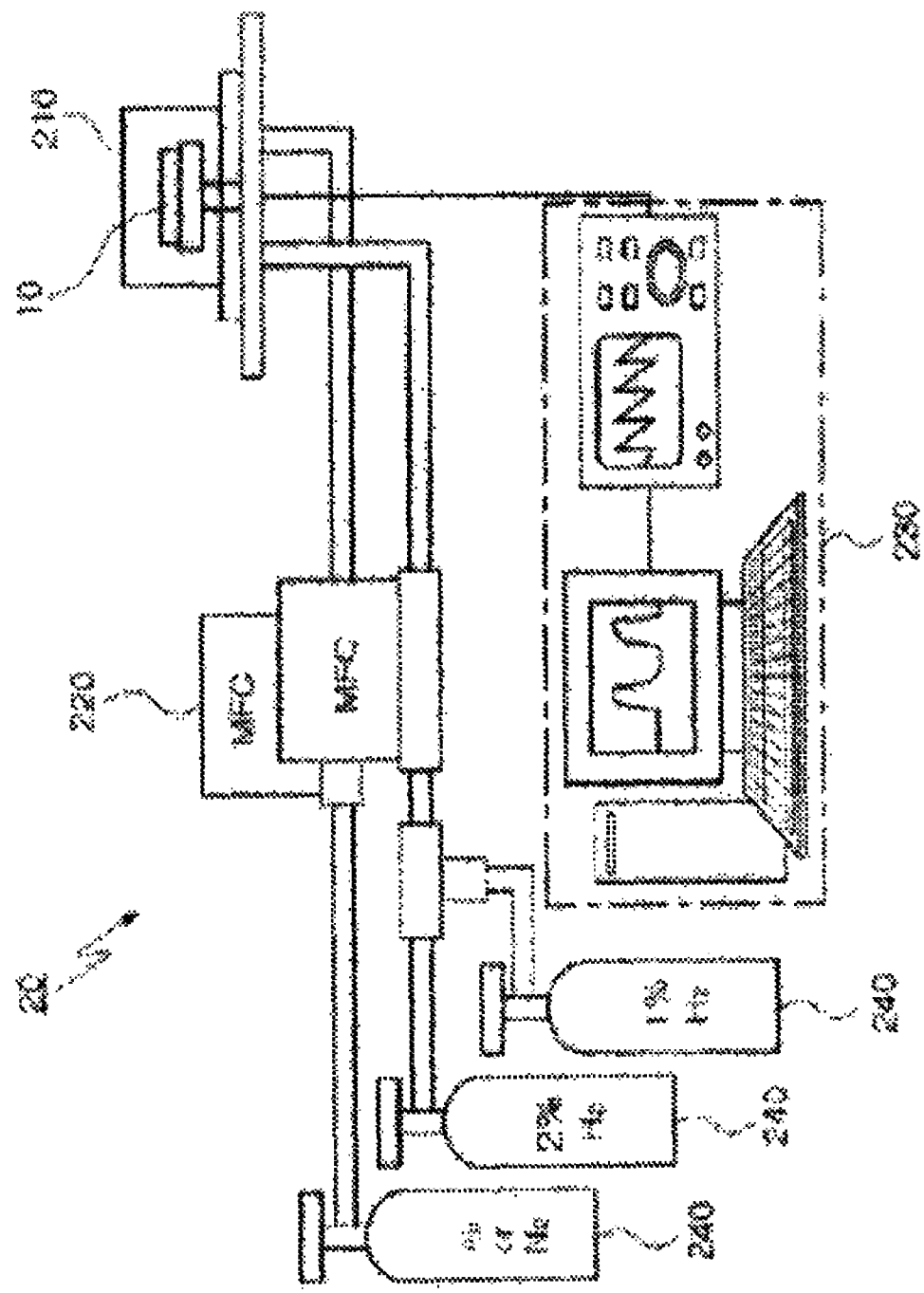
FIG. 6 is a schematic view showing a system for measuring the ability to detect hydrogen of the hydrogen sensor of the present invention.

The system is the I-V measuring device shown in FIG. 6, and includes a reaction chamber 210, which surrounds the hydrogen sensor 10 according to the manufacturing examples; a Mass Flow Controller (MFC) 220, which controls the flow rate of $H_2$ and $N_2$ gases; a device 230 for inducing a voltage and current to the sensor; and a gas tank 240.

In the system 20, the reaction chamber 210, inside of which the hydrogen sensor 10 is mounted, serves to seal the sensor from the outside when the sensor reacts with hydrogen gas, and the amounts of the $H_2$ and $N_2$ gases are precisely controlled through the MFC 220, so that the concentration of the $H_2$ gas can have an intended ratio. The $H_2$ gas, the concentration of which is controlled, reacts with the hydrogen sensor inside the reaction chamber 210, and at this time, electrical signals in response to changes in the sensor are measured by the voltage and current inducing device 230.

The measurement was carried out at room temperature and ambient pressure. After Pd thin film hydrogen sensor 10 having the nanogaps 11 therein was mounted inside the reaction chamber 210, which was connected to an external current-inducing device, a difference in the resistance was measured based on changes in the potential difference measured by inducing a current of 100 nA while flowing a mixture of $H_2$ and $N_2$ gases into the chamber.

Figure 7:
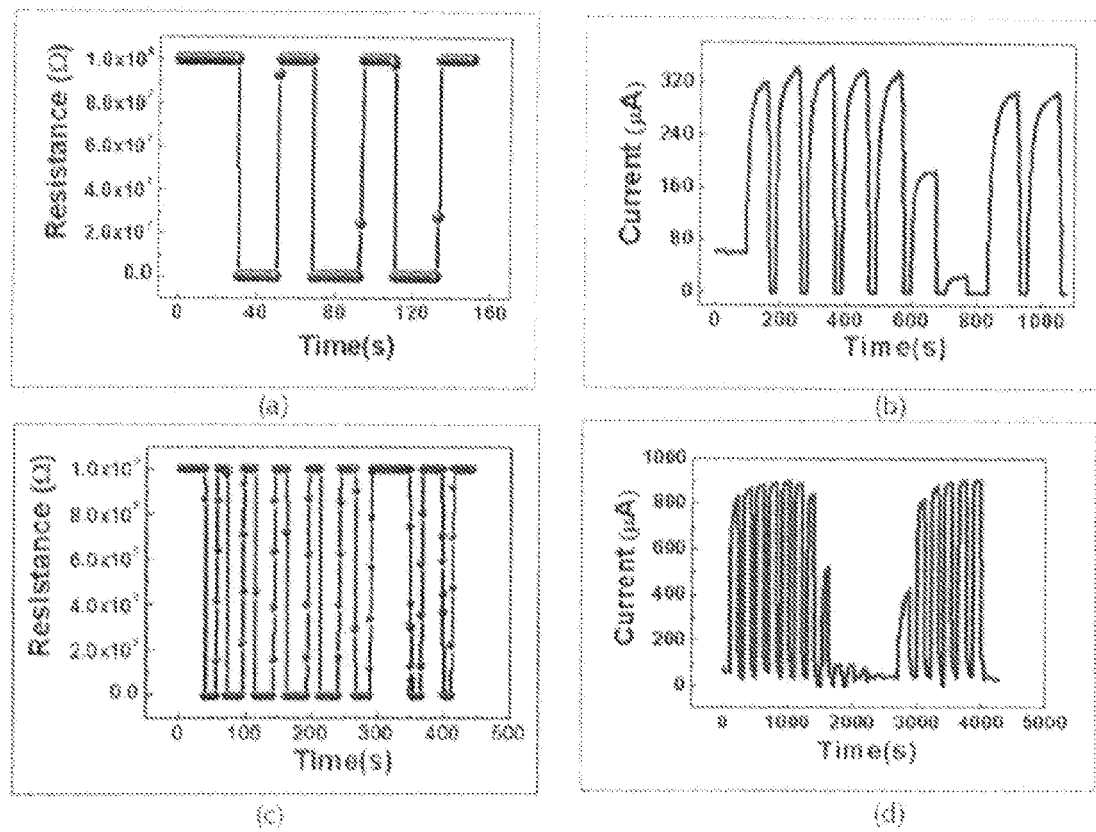
FIG. 7 is a view showing changes in the resistance value and current value measured at various concentrations of hydrogen using hydrogen sensors according to an embodiment of the invention mounted to a measuring system.

FIG. 7 (a) is a graph showing the result obtained by measuring changes in the resistance value at a concentration of hydrogen of 4% (40000 ppm) by mounting the hydrogen sensor 10, which was manufactured in Manufacturing Example 1, to the system 20 shown in FIG. 6, and FIG. 7 (b) is a graph showing current values, which were measured when the hydrogen sensor of Manufacturing Example 1 was exposed to concentrations of hydrogen ranging from 0% to 4%.

Referring to FIGS. 7 (a) and (b), it can be appreciated that the hydrogen sensor 10 of Manufacturing Example 1 exhibited an abrupt change in the resistance only in about 1 second (one dot on the graph indicates 1 second) at the concentration of hydrogen of 4%, which is the upper limit concentration before explosion, in which the resistance value increased at the moment when the hydrogen was removed from the reaction chamber 210. The hydrogen sensor 10 of Manufacturing Example 1 can operate as a precision hydrogen sensor that can detect changes in the concentration of hydrogen in ON-OFF mode.

In addition, FIG. 7 (c) is a graph showing the hydrogen sensor manufactured in Manufacturing Example 2, and FIG. 7 (d) is a graph showing the result obtained by measuring changes in the resistance value or the current value in response to changes in the concentration of hydrogen by mounting the hydrogen sensor manufactured in Manufacturing Example 3 to the system 20 shown in FIG. 6.

Referring to FIG. 7 (c), it can be appreciated that the hydrogen sensor of Manufacturing Example 2 can operate as a precision hydrogen sensor, which can detect changes in the concentration of hydrogen ranging from 0% to 4% in ON-OFF mode. Referring to FIG. 7 (d), it can be appreciated that the hydrogen sensor of Manufacturing Example 3 can also operate as a hydrogen sensor, since it exhibits changes in the resistance value in response to changes in the concentration of hydrogen.

Figure 8:
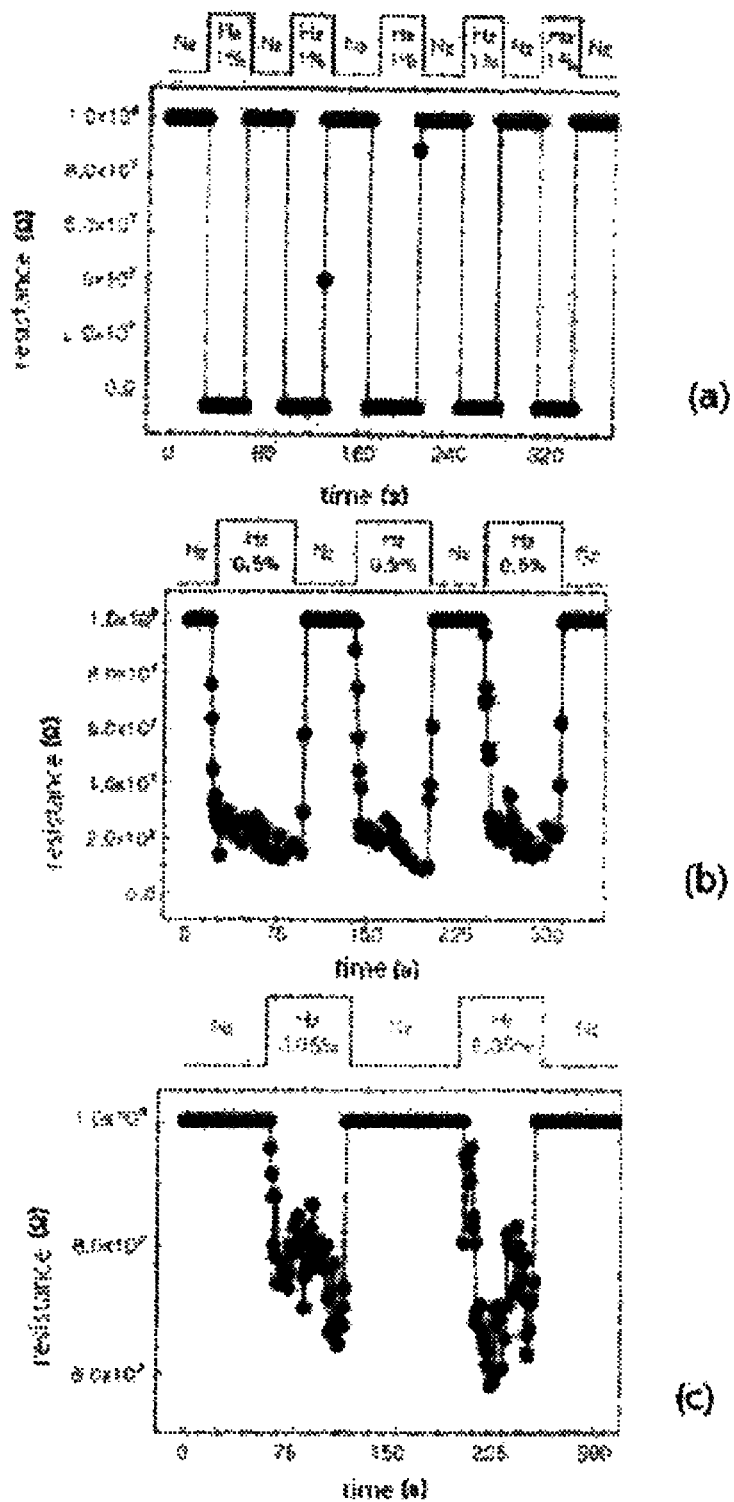
FIG. 8 is a view showing changes in the resistance at various concentrations measured using a hydrogen sensor according to an embodiment of the invention mounted to a measuring system, in which (a) is a graph showing the result obtained by measuring changes in the resistance at a concentration of hydrogen of 10000 ppm, (b) is a graph showing the result obtained by measuring changes in the resistance at a concentration of hydrogen of 5000 ppm, and (c) is a graph showing the result obtained by measuring changes in the resistance at a concentration of hydrogen of 500 ppm.

FIG. 8 is a graph showing the result obtained by measuring changes in the resistance by changing the concentration of hydrogen to 1% (10000 ppm) (a), 0.5% (5000 ppm) (b), and 0.05% (500 ppm) (c) by mounting the hydrogen sensor 10 manufactured in Manufacturing Example 4 to the system 20 shown in FIG. 6.

Referring to FIG. 8 (a), it can be appreciated that abrupt changes in the resistance occur in only about 1 second at a concentration of hydrogen of 1% (10,000 ppm), which is ¼ of the upper limit concentration before explosion (the x axis indicates overall response time). That is, it can be appreciated that the sensor can detect hydrogen gas very rapidly when compared to existing hydrogen sensors, and has very good endurance such that no changes in the magnitude of signals occur even after repeated trials.

In addition, it can be appreciated that the recovery rate was high, since the resistance value increased at a rapid speed of about 1 or 2 seconds when the hydrogen inside the reaction chamber 210 was removed.

Referring to FIG. 8 (b), it can be appreciated that abrupt changes in the resistance occur in only about 3 to 5 seconds at a concentration of hydrogen of 0.5% (5,000 ppm) such that hydrogen could be detected at high speed. It can also be appreciated that the hydrogen sensor of the invention exhibited better performance in detecting hydrogen gas, since the measured recovery time was about 3 seconds.

In addition, referring to FIG. 8 (c), pertaining to the amount of hydrogen for that was initially detected, which can be regarded as the most important factor of a sensor, the hydrogen sensor exhibited a characteristic in that it promptly detected a faint amount of hydrogen by detecting hydrogen gas in only about 3 to 5 seconds at a concentration of hydrogen of 0.05% (500 ppm). In addition, it could be appreciated that the recovery rate was high, since the resistance value increased in only 1 second when the hydrogen inside the reaction chamber 210 was removed.

Figure 9:
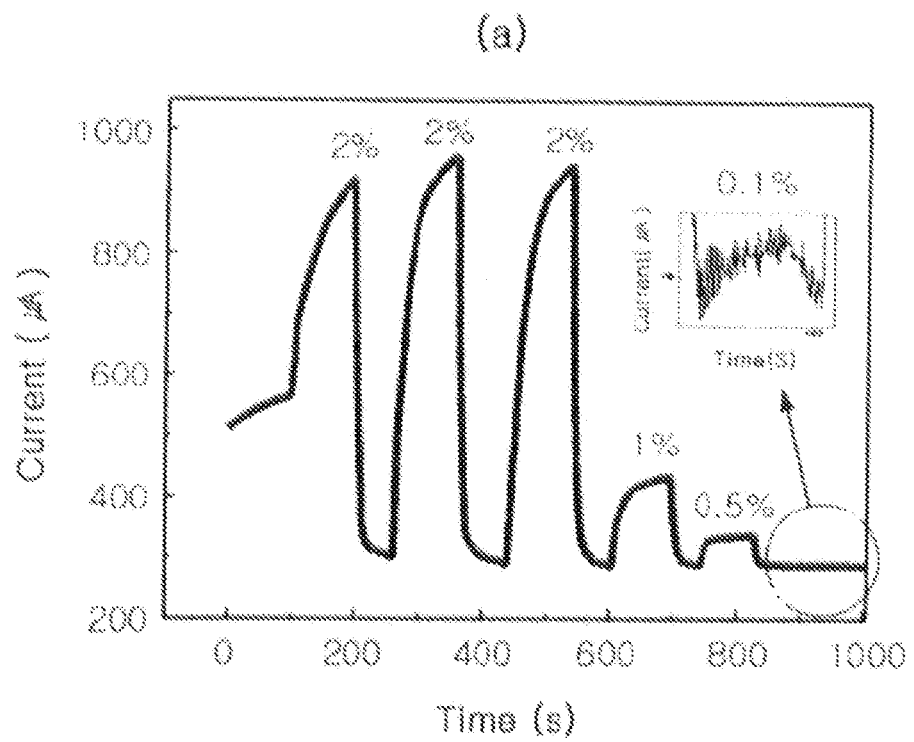
FIG. 9 is a view showing current values measured when Pd thin film hydrogen sensors according to an embodiment of the invention, which are mounted to a measuring system, are then exposed to the air, in which (a) is a graph showing current values measured using a Pd thin film hydrogen sensor having a film thickness of 16 nm, which is mounted to the measuring system and is then exposed to the air, and (b) is a graph showing current values over time measured when a Pd thin film hydrogen sensor having a film thickness of 14 nm is exposed to the air.
Figure 9:
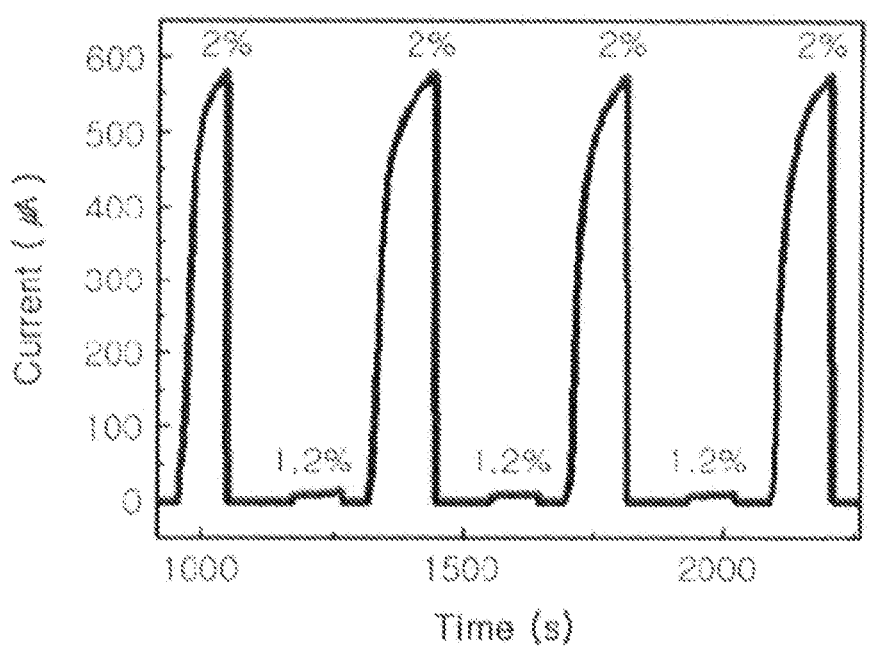

In the meantime, FIG. 9 (a) is a graph showing current values when a Pd thin film hydrogen sensor having a film thickness of 16 nm according to another manufacturing example of this embodiment is exposed to the air, and FIG. 9 (b) is a graph showing changes in the current value over time when a Pd thin film hydrogen sensor having a film thickness of 14 nm is exposed to the air. As shown in FIG. 9 (a), it can be appreciated that, if the Pd thin film is thick with the thickness of 16 nm, the hydrogen sensor operates as an ON sensor, the base resistance of which does not drop to 0, in the air. In contrast, as shown in FIG. 9 (b), it can be appreciated that, if the Pd thin film is thin with the thickness of 14 nm, the hydrogen sensor operates as an ON-OFF sensor, the base resistance of which drops to 0, in the air after early several reactions.

Figure 10:
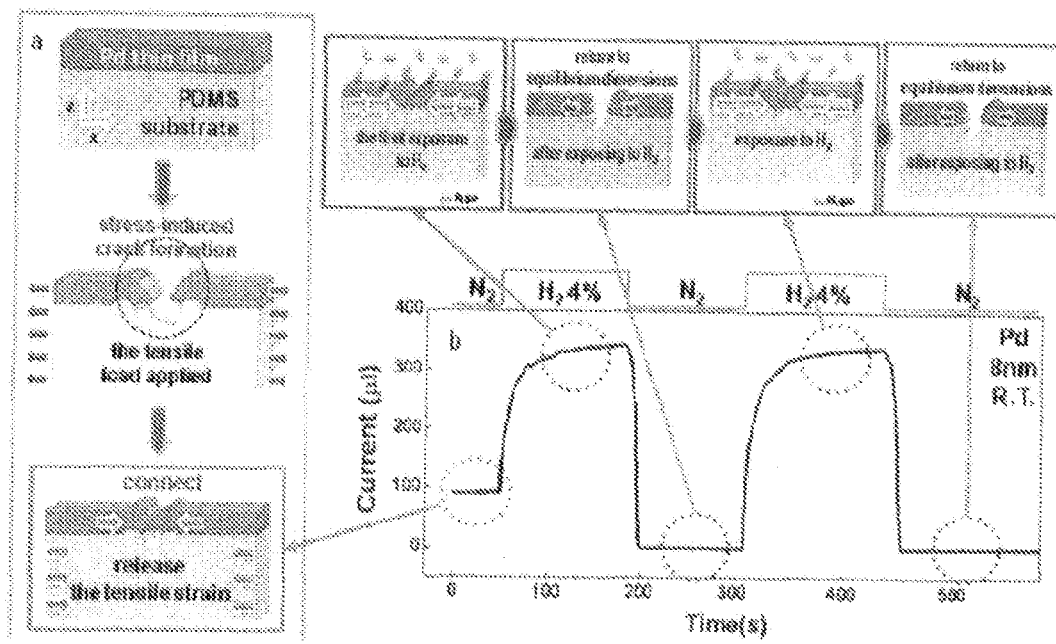
FIG. 10 is a view showing the mechanism that occurs when a Pd thin film hydrogen sensor is repeatedly exposed to hydrogen and a graph showing changes in the current value over time when a Pd thin film hydrogen sensor having a film thickness of 8 nm is exposed to the air.

In addition, FIG. 10 shows the mechanism that occurs when a hydrogen sensor of this embodiment is exposed to $N_2$ gas or to the air, and a graph showing changes in the current value over time when a Pd thin film hydrogen sensor having a film thickness of 8 nm is exposed to the air. As shown in FIG. 10, it can be appreciated that the hydrogen sensor operates as an ON-OFF sensor. Specifically, the ON-OFF hydrogen sensor stays in an "ON" state, in which the base resistance does not drop to zero (0), when nanocracks are formed in the Pd thin film by stretching. When the sensor is exposed to hydrogen, the resistance decreases in response to expansion. When all of the hydrogen is removed, the sensor changes into an "OFF" state in response to the transition into the state of thermodynamic equilibrium. As an illustrative example, changes in the resistance value over time are shown when a PD thin film hydrogen sensor having a film thickness of 8 nm is exposed to nitrogen.

2. Embodiment B

In the foregoing embodiment, the manufacturing of a hydrogen sensor using a transition metal or an alloy thereof has been described. In this embodiment, the manufacturing of a hydrogen sensor using a thin film made of a $Pd_xNi_{1-x}$ alloy, which is selected from among the foregoing transition metals, is described in greater detail. Since the details of this embodiment are the same as those described in Embodiment A, except that the thin film made of a $Pd_xNi_{1-x}$ alloy is formed on the elastic substrate, descriptions of the same or like parts will be omitted.

First, in order to manufacture the hydrogen sensor of the invention, a thin film made of a $Pd_xNi_{1-x}$ alloy is formed on an elastic substrate. Although the alloy thin film can be formed by a plurality of methods, in this embodiment, it is formed by the following method. That is, FIG. 11 schematically shows two methods of forming the thin film made of a $Pd_xNi_{1-x}$ alloy according to this embodiment.

Figure 11:
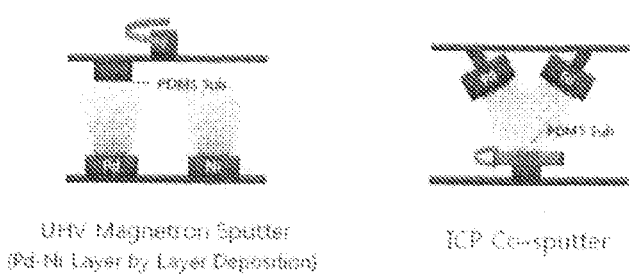
FIG. 11 is a view schematically showing two methods of forming a $Pd_xNi_{1-x}$ alloy film on a substrate according to an embodiment of the invention.

The left part of FIG. 11 shows a layer-by-layer type, in which two targets (Pd and Ni) are positioned parallel to each other, and a sample holder rotates so as to alternately pass over the two targets with time intervals. Thereby, Pd and Ni are deposited on the substrate in a layer-by-layer pattern. In the meantime, it can be appreciated that the right part of FIG. 11 is different from the former type. Specifically, two targets are provided at an incline so that two kinds of plasma generated from the two targets overlap each other around a sample holder, which is positioned below the targets. Since the sample holder is rotating, two target materials are uniformly deposited on the substrate. Since the two materials are simultaneously deposited, Pd and Ni form an alloy or a solid solution, unlike the former type. The thin films made of a $Pd_xNi_{1-x}$ alloy are formed using the above-described methods, and there is no difference in the hydrogen detection characteristics, which will be described later, regardless of the thin film deposition methods. In the meantime, it should be understood that the invention is not limited to the above-described deposition methods. That is, the $Pd_xNi_{1-x}$ alloy deposition methods are merely illustrative examples of the method of depositing the $Pd_xNi_{1-x}$ alloy on the substrate, and the invention is not limited to specific methods of depositing the $Pd_xNi_{1-x}$ alloy. For example, as described in Embodiment A, sputtering, Chemical Vapor Deposition (CVD), Atomic Layer Deposition (ALD), and the like can be used.

Figure 12:
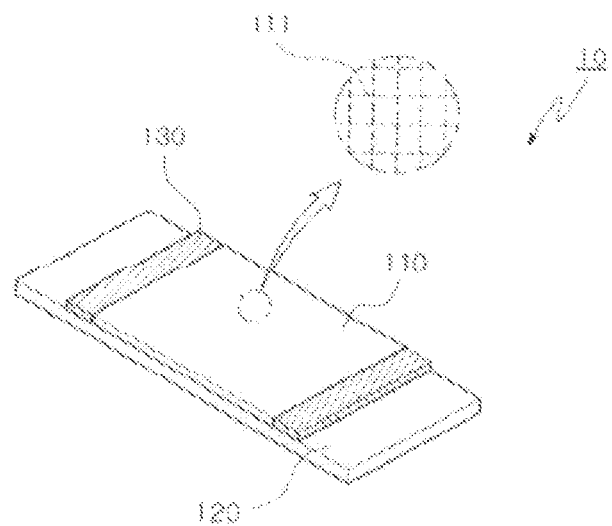
FIG. 12 is a perspective view showing a hydrogen sensor according to an embodiment of the invention.

FIG. 12 is a perspective view showing a hydrogen sensor of this embodiment. The hydrogen sensor 10 includes a substrate 120 made of an elastic material; a $Pd_xNi_{1-x}$ alloy thin film 110 formed on the surface of the substrate 120, the thin film 110 having a plurality of nanogaps 111 formed by a tensile force that is applied to the substrate 120; and electrodes 130 formed on opposite ends of the thin film. Unlike Embodiment A, the thin film 110 made of the $Pd_xNi_{1-x}$ alloy, which satisfies the relationship: $0.85 \leq x \leq 0.96$, is formed on the substrate 120 of this embodiment. In this embodiment, the $Pd_xNi_{1-x}$ alloy thin film, which has a predetermined composition, is formed in place of the Pd thin film, which is typically used in the hydrogen sensors of the related art, for the following specific reasons.

Specifically, when the Pd thin film is exposed to a predetermined concentration of hydrogen, it undergoes phase transition, in which its phase changes at a specific concentration or more. When nanogaps are formed by the stretching and are exposed to hydrogen, a reaction occurs only if the hydrogen is at a concentration, with which the distances between the gaps decrease, or hither. This is caused by the phase transition of Pd, and has a disadvantage in that the lowest detectable concentration becomes very high.

In the case in which the $Pd_xNi_{1-x}$ alloy thin film is used as proposed in this embodiment instead of the PD thin film, it was found that the problem of deterioration in the ability to detect hydrogen gas can be overcome, since phase transition, which is attributable to the difference in the concentration of exposed hydrogen, does not occur. In this embodiment, in consideration of such factors, the $Pd_xNi_{1-x}$ alloy thin film 110 that satisfies the relationship: $0.85 \leq x \leq 0.96$ is formed on the elastic substrate 120. If the molar ratio x is less than 0.85, the problem in which the strength of the reaction in response to the leakage of hydrogen decreases due to excessive Ni content occurs. If the molar ratio x exceeds 0.96, the above-described problem of phase transition occurs. It is further preferable that the molar ratio be $0.90 \leq x \leq 0.94$.

Subsequently, the nanogaps 111 are formed in the alloy thin film 110 formed on the surface of the substrate by applying a tensile force to the elastic substrate 120. Other factors, such as Poisson's ratio, the material of the elastic substrate, the tensile force applied to the elastic substrate, the number of times that the tensile force is applied, the direction of the tensile force, the thickness of the alloy thin film, and the width of the nanogaps, are the same as those of Embodiment A, and thus repeated descriptions thereof are omitted.

Like the hydrogen sensor of Embodiment A, the hydrogen sensor manufactured according to this embodiment can reduce power consumption, since it can measure hydrogen at room temperature and has a small size, unlike existing hydrogen sensors. Therefore, the hydrogen sensor according to this embodiment can realize factors that are required of sensors, such as reduced response time and stable operation, while satisfying characteristics such as low price, small size, low power consumption, and operation at room temperature.

Below, experimental examples of this embodiment are described in detail.

A $Pd_xNi_{1-x}$ alloy (where $0.85 \leq x \leq 0.96$) was deposited, via sputtering, on a PDMS substrate 120 having a width of 20 mm, a length of 10 mm, and a thickness of 0.75 mm. Here, the $Pd_xNi_{1-x}$ thin film having a thickness of 7.5 nm, a width of 15 mm, and a length of 10 mm was disposed on the substrate.

Figure 13:
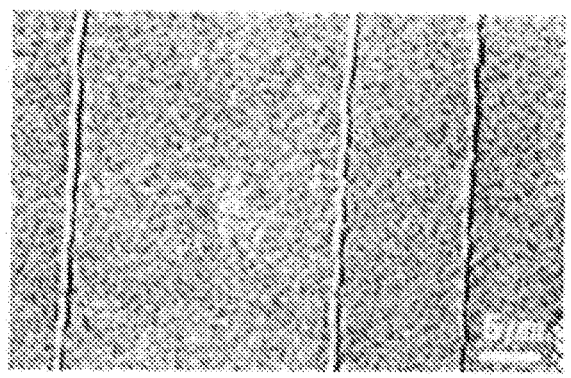
FIG. 13 is a Scanning Electron Microscope (SEM) image picture of a $Pd_xNi_{1-x}$ alloy film having nanogaps formed therein.
Figure 14:
FIG. 14 is an optical image picture of a $Pd_xNi_{1-x}$ alloy film having nanogaps formed therein.

Afterwards, the substrate was stretched by applying a tensile force five times to the substrate so that the width became 25 mm, and then the tensile force was removed. In this fashion, nanogaps were formed in the $Pd_xNi_{1-x}$ thin film. FIG. 13 is a Scanning Electron Microscope (SEM) image picture of the $Pd_xNi_{1-x}$ alloy thin film having the nanogaps, which were formed through the above-described process, and FIG. 14 is an optical image picture of the $Pd_xNi_{1-x}$ alloy thin film having the nanogaps.

In addition, for the purpose of comparison, Pd was deposited on a PDMS substrate having the same size as above via sputtering. Here, the Pd thin film having a thickness of 7.5 nm, a width of 15 mm, and a length of 10 mm was disposed on the substrate. Afterwards, the substrate was stretched by applying a tensile force five times to the substrate so that the width became 25 mm, and then the tensile force was removed. In this fashion, nanogaps were formed in the Pd thin film.

The thin films having therein the nanogaps formed through the two processes described above were subjected to sputtering so that Au electrodes were deposited on opposite ends of each thin film. Thereby, hydrogen sensors, each having the thin film and the electrodes, which are provided on the PDMS substrate and electrically connected to each other, were manufactured.

In order to evaluate the characteristics of the hydrogen sensor manufactured above, the measuring system 20 shown in FIG. 6, which can perform measurement using a quasi-two probe method, was used, as in Embodiment A. A description of this system is omitted, since it is described in Embodiment A.

The measurement using this system was performed at room temperature and ambient pressure. After the $Pd_xNi_{1-x}$ thin film hydrogen sensor 10 having the nanogaps therein was mounted inside the reaction chamber 210, which was connected to an external current-inducing device, the intensity of current was measured with the voltage fixed at 0.1V while flowing a mixture of $H_2$ and $N_2$ gases into the chamber.

Figure 15:
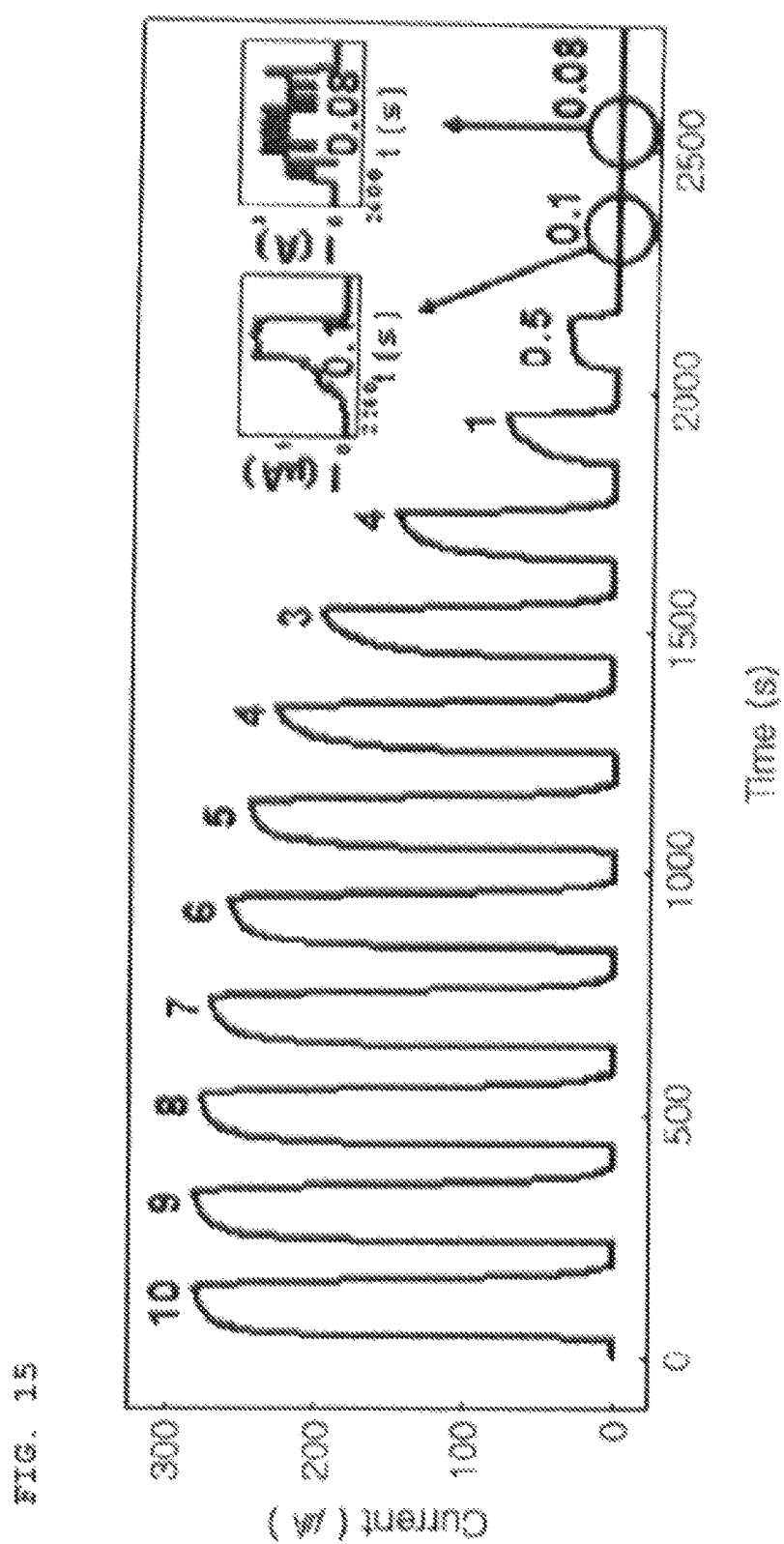
FIG. 15 is a graph showing current values measured when a $Pd_{93}Ni_7$ alloy thin film hydrogen sensor having a film thickness of 7.5 nm according to an embodiment of the invention, which is mounted to a measuring system, is exposed to nitrogen gas.
Figure 16:
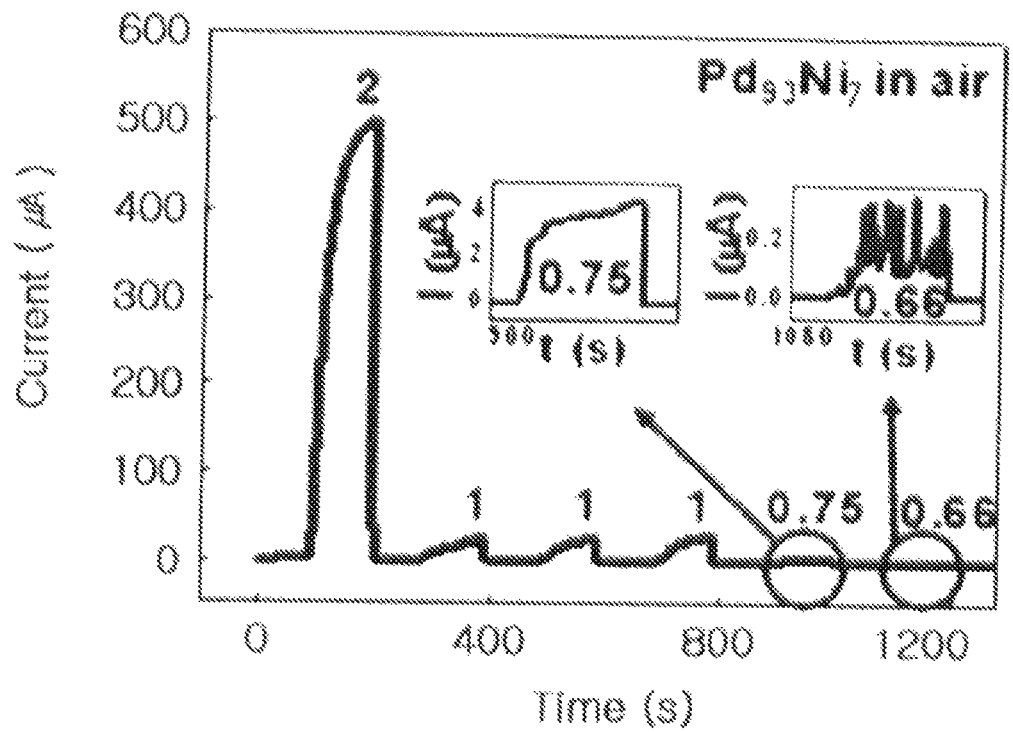
FIG. 16 is a graph showing current values measured when a $Pd_{93}Ni_7$ alloy thin film hydrogen sensor having a film thickness of 7.5 nm according to an embodiment of the invention, which is mounted to a measuring system, is exposed to the air.

As shown in FIG. 15, it can be appreciated that the minimum concentration of hydrogen detected was about 0.08% when the hydrogen sensor having a thin film made of a $Pd_{93}Ni_7$ alloy was exposed to nitrogen. As shown in FIG. 16, it can be appreciated that the minimum concentration of hydrogen detected showed a very low value of 0.66% when the sensor was exposed to the air.

Figure 17:
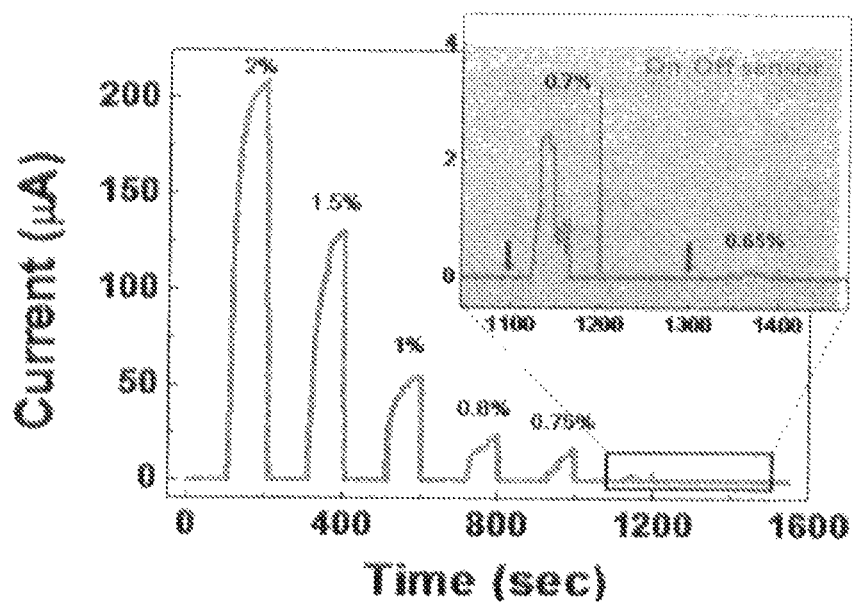
FIG. 17 is a graph showing current values measured when a $Pd_{93}Ni_7$ alloy thin film hydrogen sensor having a film thickness of 8 nm, which is mounted to a measuring system, is exposed to the air.
Figure 18:
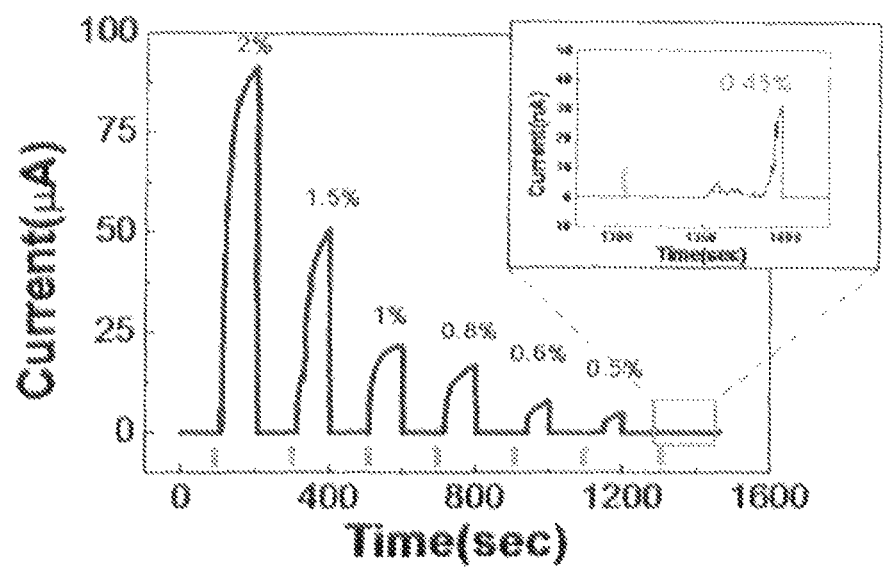
FIG. 18 is a graph showing current values measured when a $Pd_{93}Ni_7$ alloy thin film hydrogen sensor having a film thickness of 10 nm, which is mounted to a measuring system, is exposed to the air.
Figure 19:
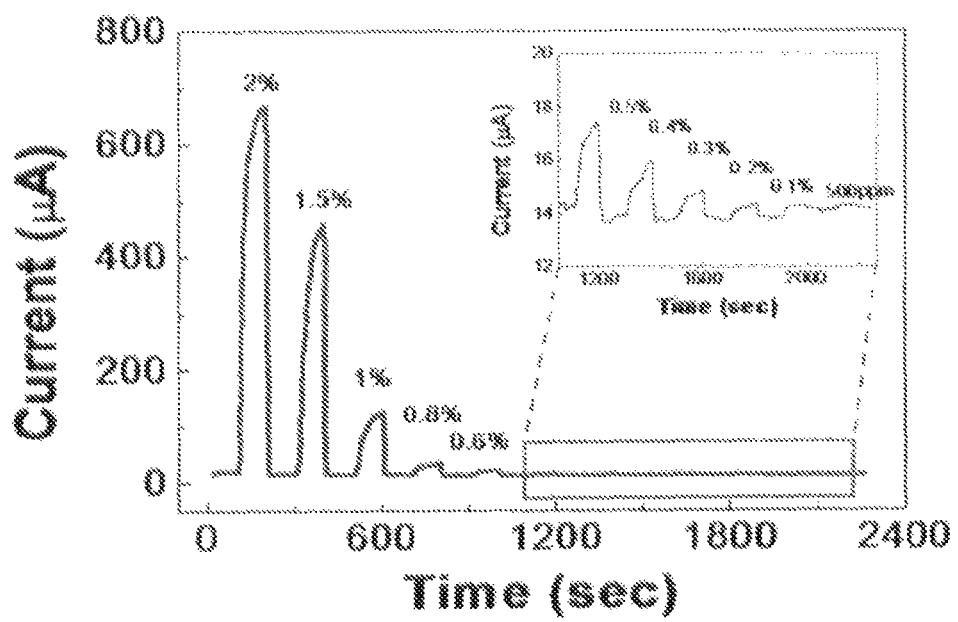
FIG. 19 is a graph showing current values measured when a $Pd_{93}Ni_7$ alloy thin film hydrogen sensor having a film thickness of 11 nm, which is mounted to a measuring system, is exposed to the air.

In the meantime, the inventor carried out experiments following the above-described processes by changing the thickness of the thin film having the above-described composition, which was formed on the substrate, and the results are presented in FIGS. 17 to 21. Specifically, FIGS. to 19 show the concentrations of hydrogen that were detected when the hydrogen sensors, with the thin films formed at respective thicknesses of 8 nm, 10 nm, and 11 nm, were exposed to the air inside the reaction chamber 210. As shown in the figures, it can be appreciated that the minimum concentration of hydrogen detected was further lowered compared to FIG. 16. In FIG. 17, the minimum concentration of hydrogen detected is 0.65%, i.e. 6500 ppm, and in FIG. 18, the minimum concentration of hydrogen detected is about 0.45%. In FIG. 19, the minimum concentration of hydrogen detected is 500 ppm; this means that a faint amount of hydrogen can be detected. It can be understood that the thicker the film having the above-described composition is, the lower the concentration of hydrogen that can be detected is.

Figure 20:
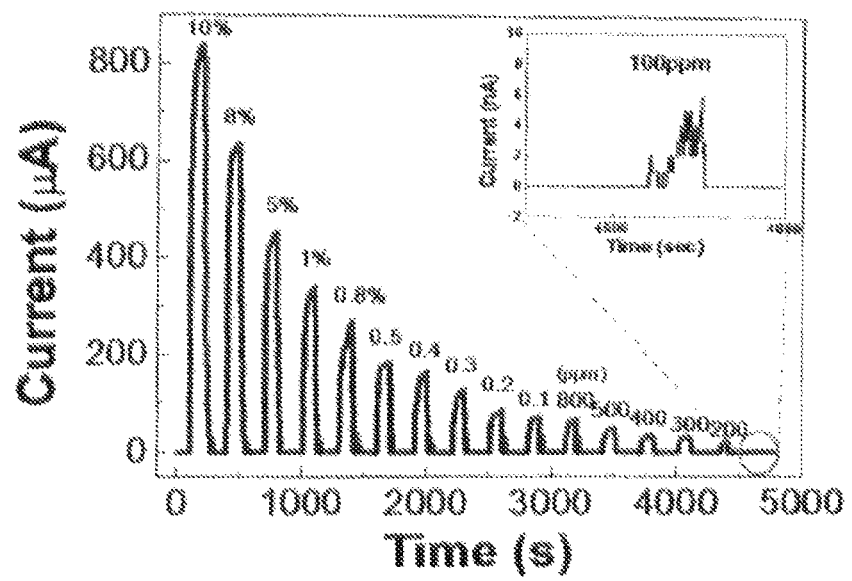
FIG. 20 is a graph showing current values measured when a $Pd_{93}Ni_7$ alloy thin film hydrogen sensor having a film thickness of 10 nm, which is mounted to a measuring system, is exposed to nitrogen gas.
Figure 21:
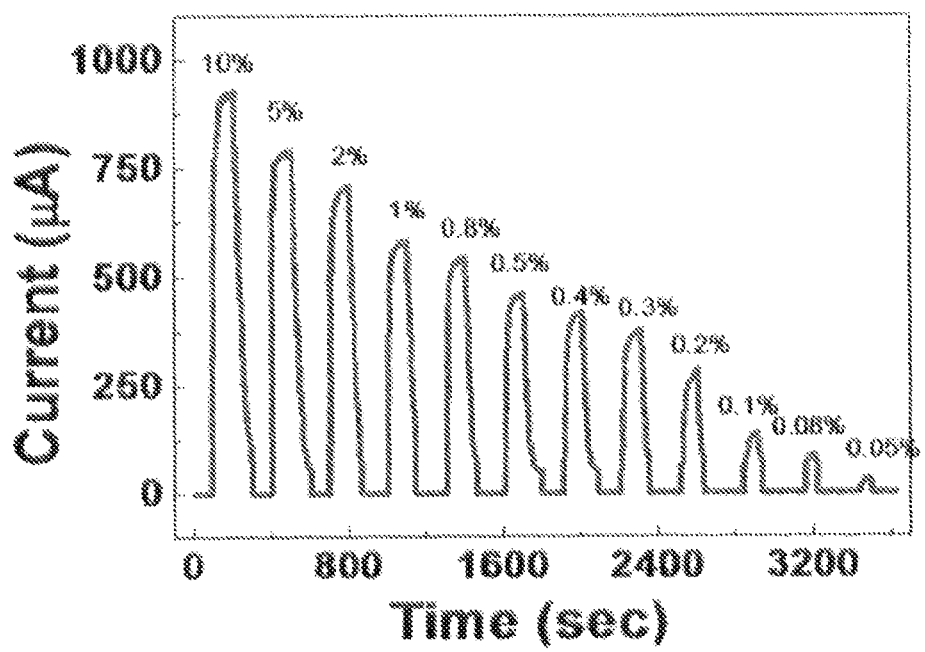
FIG. 21 is a graph showing current values measured when a $Pd_{93}Ni_7$ alloy thin film hydrogen sensor having a film thickness of 11 nm, which is mounted to a measuring system, is exposed to nitrogen gas.

FIGS. 20 and 21 are views showing the concentrations of hydrogen that were detected when the hydrogen sensors, with thin films formed at respective thicknesses of 10 nm and 11 nm, were exposed to the nitrogen atmosphere inside the reaction chamber 210. In FIG. 20, the minimum concentration of hydrogen detected is about 0.01%, and in FIG. 21, the minimum concentration of hydrogen detected is about 0.05%. It can be appreciated that the minimum concentration of hydrogen detected is lower than that is detected in the air.

Figure 22:
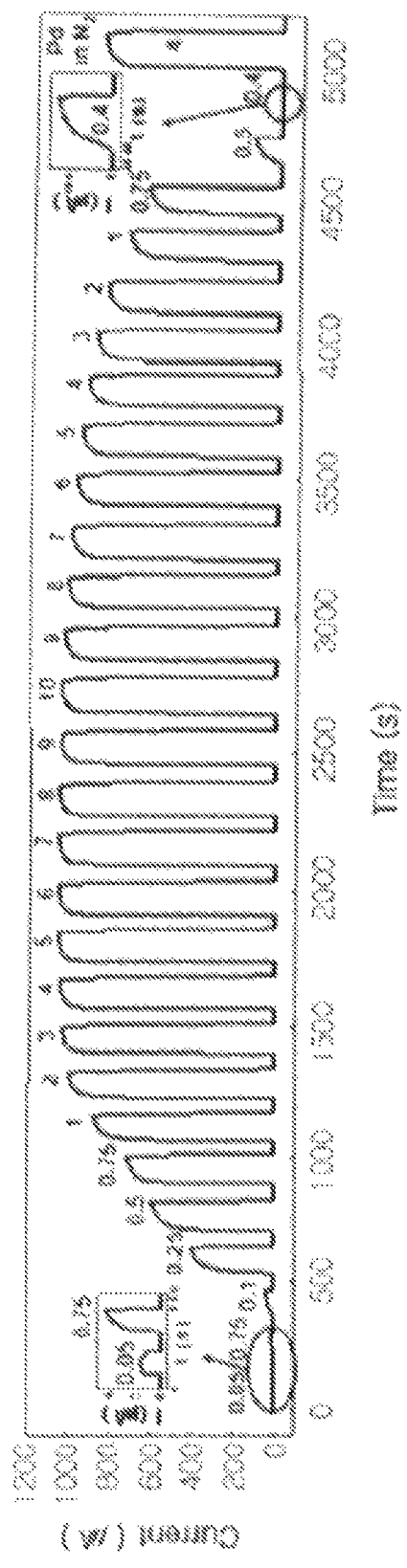
FIG. 22 is a graph showing current values measured when a Pd thin film hydrogen sensor having a film thickness of 7.5 nm according to a comparative example of the invention, which is mounted to a measuring system, is exposed to the nitrogen gas.
Figure 23:
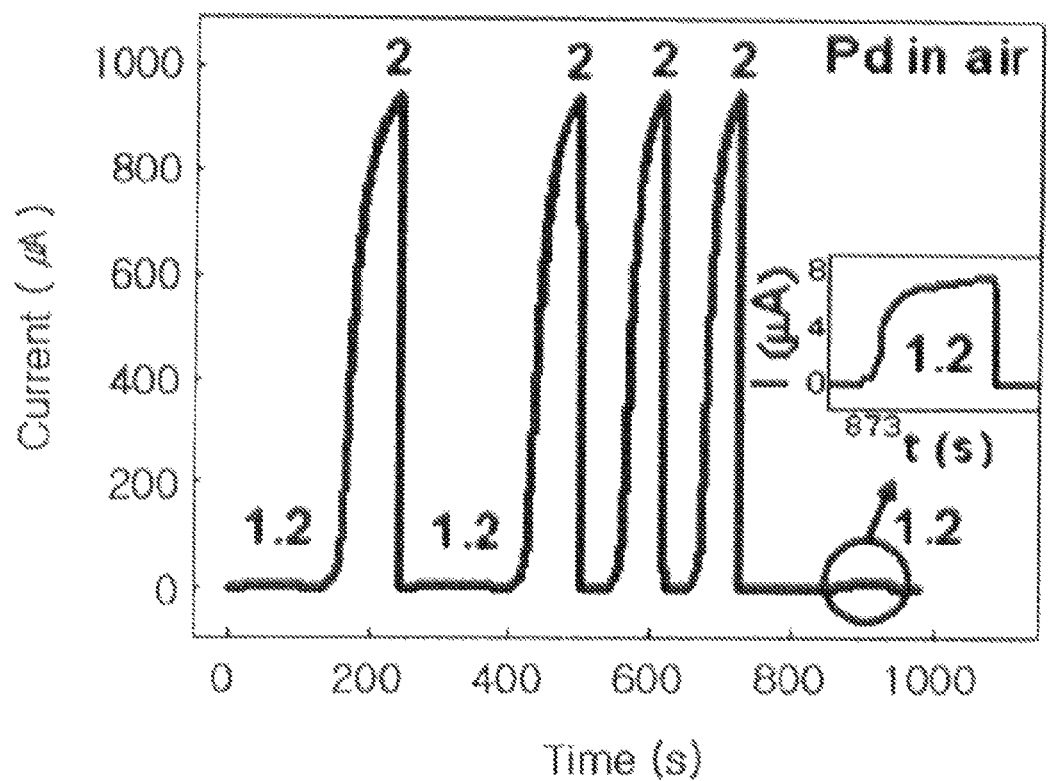
FIG. 23 is a graph showing current values measured when a Pd thin film hydrogen sensor having a film thickness of 7.5 nm according to a comparative example of the invention, which is mounted to a measuring system, is exposed to the air.

Compared to the experimental examples of this embodiment described above, as shown in FIG. 22, when the hydrogen sensor having a Pd thin film (with a thickness of 7.5 nm) was exposed to nitrogen, the minimum concentration of hydrogen detected is 0.4%. As shown in FIG. 23, when the sensor was exposed to the air, the minimum concentration of hydrogen detected is 1.2%. It can be appreciated that the concentration of hydrogen detected is higher compared to the $Pd_xNi_{1-x}$ alloy that has a composition of the invention.

As described above, it can be understood that, when the $Pd_xNi_{1-x}$ alloy thin film having a predetermined composition of the invention is used in the hydrogen sensor, phase transition caused by the exposure to hydrogen is reduced so that this hydrogen sensor can detect a significantly lower concentration of hydrogen compared to the hydrogen sensor to which the Pd thin film is applied.

3. Embodiment C

In the foregoing Embodiments A and B, the nanogaps were formed in the thin film formed on the elastic substrate by applying a tensile force to the elastic substrate, and hydrogen was detected using the nanogaps. In the following embodiment, a description will be given of the detection of hydrogen by forming nanogaps using a mechanism rather different from that applying a tensile force, but descriptions of the components and functions the same as those of Embodiments A and B will be omitted.

Figure 24:
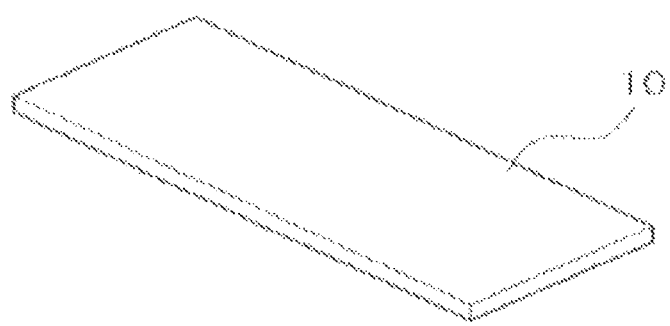
FIG. 24 is a is a view showing a process of manufacturing a hydrogen sensor according to an embodiment of the invention.
Figure 24:
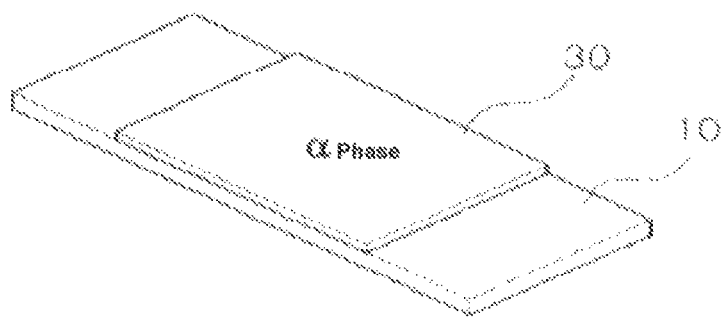
Figure 24:
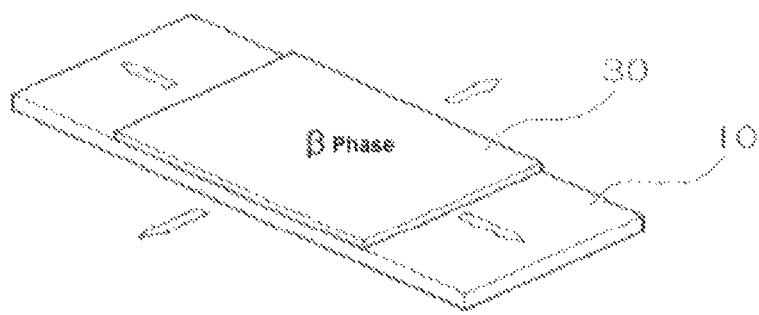
Figure 24:
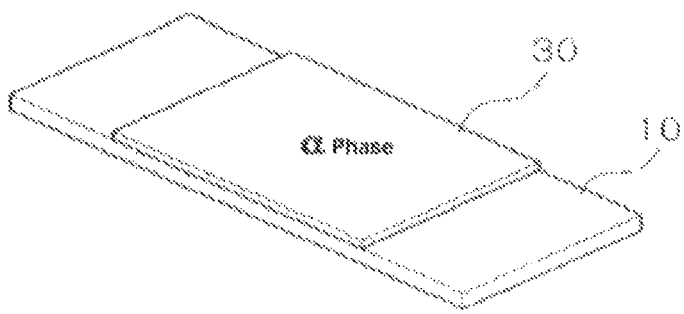

FIG. 24 is a view showing a process of manufacturing a hydrogen sensor according to this embodiment. As shown in FIG. 24 (*a*), also in this embodiment, an elastic substrate 10 is first prepared as in the foregoing embodiments. The elastic substrate 10 serves to accommodate an expansion in the volume of a Pd or Pd-alloy thin film formed on the elastic substrate in response to phase transition, thereby promoting the formation of nanogaps in the thin film.

The present invention is not specifically limited as to the composition or type of the elastic substrate 10, and various types of elastic material, which can accommodate the volumetric expansion and contraction caused by the phase transition of the Pd or Pd-alloy thin film formed on the upper surface of the substrate, can be used. For example, like the foregoing Embodiments A and B, the elastic substrate can be made of natural rubber, synthetic rubber, or polymer.

Subsequently, as shown in FIG. 24 (*b*), a thin film 30 made of Pd or a Pd alloy, which has α phase, is formed on the elastic substrate 10. The method of forming the Pd or Pd-alloy thin film 30 can employ any method that is well known in the art. Like the foregoing embodiments, sputtering, Chemical Vapor Deposition (CVD), or the like can be used.

The thickness of the thin film 30 that is formed above depends on how efficiently the nanogaps are formed in the thin film 30 when the thin film 30 undergoes phase transition α<->β during the following processing. So, the thinner the film is, the higher the number of the nanogaps can be formed is. Therefore, like the foregoing embodiments, the thickness of the thin film 30 is in the range, preferably, from 1 nm to 100 μm, more preferably, from 3 nm to 100 nm, and most preferably, from 5 nm to 15 nm, such that the nanogaps can be efficiently formed in the thin film.

In this embodiment, the Pd alloy thin film may be made of one selected from among Pd—Ni, Pd—Pt, Pd—Ag, Pd—Ti, Pd—Fe, Pd—Zn, Pd—Co, Pd—Mn, Pd—Au, and Pd—W. More preferably, the Pd alloy thin film is a Pd—Ni thin film.

Subsequently, as shown in FIG. 24 (c), the thin film 30 having α phase is exposed to gas that contains a predetermined concentration of hydrogen. In response to the exposure to the hydrogen-containing gas, the α phase in the thin film 30 is gradually converted into β phase.

As shown in FIG. 24 (c), the thin film 30 undergoes volume expansion by absorbing the hydrogen, and the underlying elastic substrate 10 accommodates the volume expansion of the thin film 30. As a result, in response to the volume expansion, nanogaps in response to the volume expansion are formed inside the thin film 30 in which the phase transition to the β phase has occurred. These nanogaps can have a width ranging, approximately, from 1 nm to 10 μm. In the exposure to the hydrogen-containing gas, it is preferred that the concentration of hydrogen range from 2% to 15%. This is because the phase transition of the thin film 30 easily occurs in this range.

Figure 25:
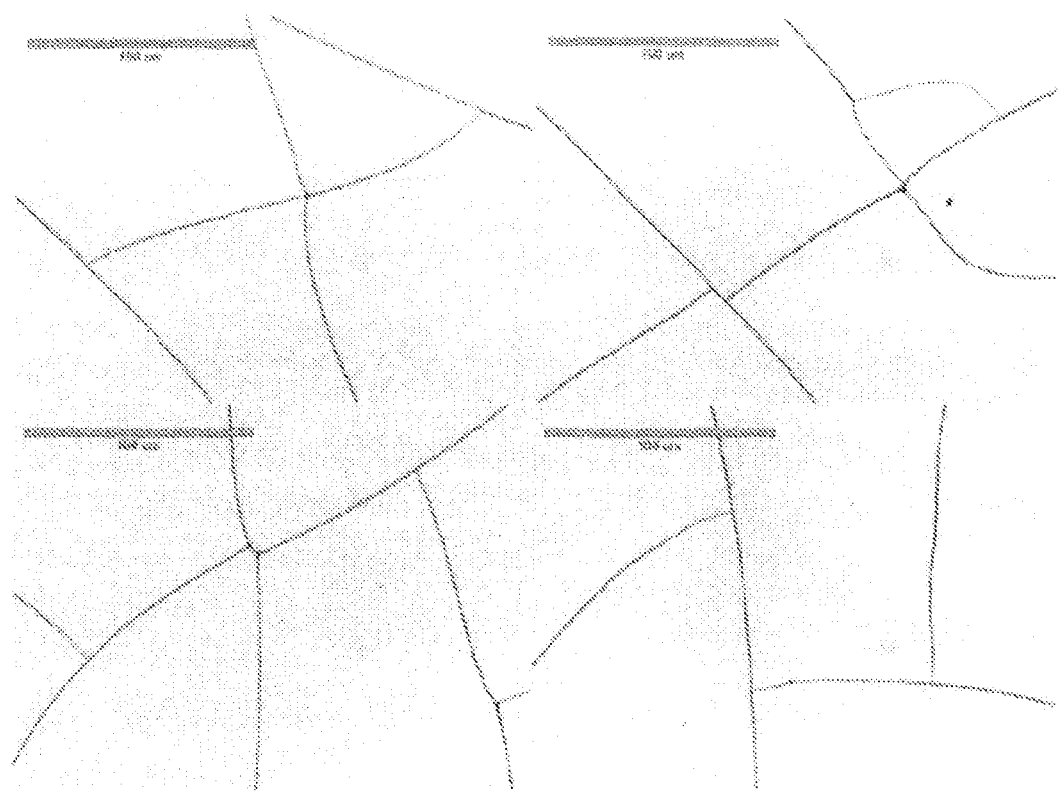
FIG. 25 is an Optical Microscope (OM) image picture of a Pd thin film having a thickness of 10 nm, which is manufactured according to an embodiment of the invention.

Afterwards, the β phase of the thin film 30 is changed into the α phase again by stopping the exposure of the thin film to the hydrogen-containing gas (see FIG. 25 (d)). Even after the change into the α phase, the nanogaps formed in response to the volume expansion still remain inside the thin film 30, so that the resultant structure can properly operate as a hydrogen sensor. The principle of the hydrogen sensor that operates in response to the volume expansion is the same as described in the foregoing embodiments. In addition, like the foregoing embodiments, it is possible to increase the surface area of the thin film 30 having the nanogaps therein via ion milling or enhance the mechanical properties of the same film via heat treatment.

Below, a detailed description will be given of this embodiment with reference to Experimental Example.

EXPERIMENTAL EXAMPLE

Pd was deposited, via sputtering, on PDMS substrates, each of which had a width of 20 mm, a length of 10 mm, and a thickness of 0.75 mm. Here, a-phase Pd thin films were formed on the substrate 120, with respective thicknesses of 10 nm and 11 nm, a width of 15 mm, and a length of 10 mm. Afterwards, the α-phase Pd thin films formed on respective PDMS substrates were exposed to a hydrogen-containing gas having a concentration of hydrogen of 10% so that the thin file undergoes phase transition to β phase. Subsequently, the β phase of the thin film 30 was converted into the α phase again by stopping the exposure of the thin film to the hydrogen-containing gas.

FIG. 25 is an Optical Microscope (OM) image picture of the Pd thin film having a thickness of 10 nm, manufactured using the above process. As shown in FIG. 25, it can be appreciated that the Pd thin film manufactured by the above process has nanogaps therein, and thus can be effectively used as a hydrogen sensor.

Subsequently, the thin films having the nanogaps therein through the process described above were subjected to sputtering so that Au electrodes were deposited on the opposite ends of each film. Thereby, hydrogen sensors, each having the thin film and the electrodes, which are formed on the PDMS substrate and are electrically connected to each other, were manufactured. In order to evaluate the characteristics of the hydrogen sensor manufactured above, the I-V measuring system shown in FIG. 6, which can perform measurement using a quasi-two probe method, was used, as in the foregoing embodiments.

The measurement was performed at room temperature and ambient pressure. After the Pd thin film hydrogen sensor 10 was mounted inside the reaction chamber 210, which was connected to an external current-inducting device, changes in current were measured by applying a current of 100 nA while flowing a mixture of $H_2$ and $H_2$ gases into the chamber.

Figure 26:
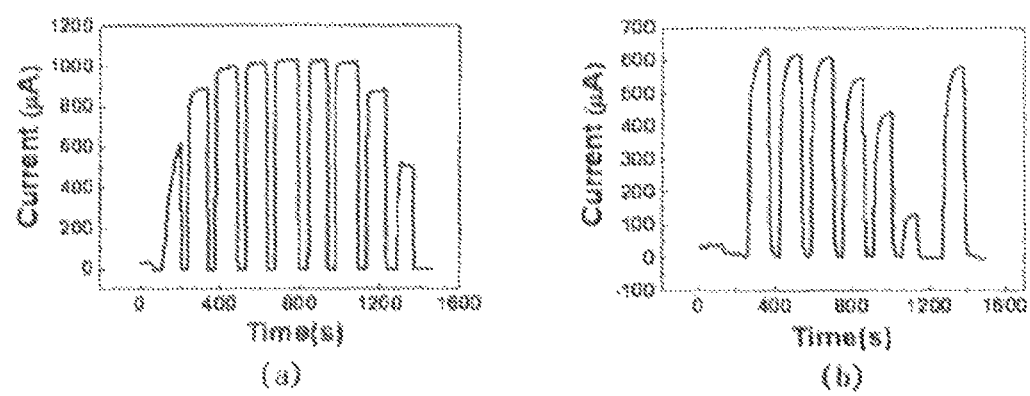
FIG. 26 (a) is a graph showing changes in the current value measured when a Pd thin film having a thickness of 10 nm is exposed to a concentration of hydrogen ranging from 0.5% to 4%, and FIG. 26 (b) is a graph showing changes in the current value measured when a Pd thin film having a thickness of 11 nm is exposed to a concentration of hydrogen ranging from 0.5% to 4%.

FIG. 26 (a) is a graph showing changes in the resistance value that were measured when the Pd thin film having a thickness of 10 nm was exposed to a concentration of hydrogen ranging from 0.5% to 4%, and FIG. 26 (b) is a graph showing changes in the current value that were measured when the Pd thin film having a thickness of 11nm was exposed to a concentration of hydrogen ranging from 0.5% to 4%. As shown in FIG. 26 (a) and (b), the hydrogen sensors manufactured according to this embodiment exhibits a current value when it is exposed to hydrogen but the current value drops to zero (0) when the hydrogen is removed. Therefore, it can be appreciated that the hydrogen sensors can operate as a precision hydrogen sensor that can detect changes in the concentration of hydrogen in On-OFF mode.

Figure 27:
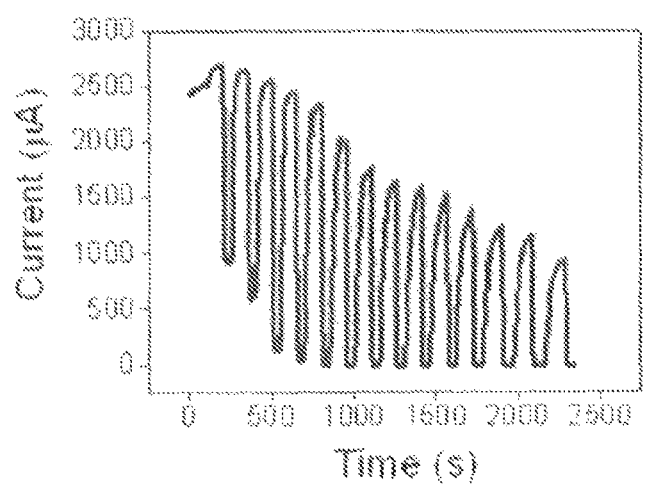
FIG. 27 is a graph showing changes in the current value measured when a Pd thin film having a thickness of 10.5 nm is exposed to a concentration of hydrogen ranging from 2%.

FIG. 27 is a graph showing changes in the current value when a Pd thin film having a thickness of 10.5 nm when the Pd thin film is being exposed to the air having a concentration of hydrogen of 2%. From this graph, it can also be appreciated that the hydrogen sensor can detect changes in the concentration of hydrogen in ON-OFF mode, since it exhibits a current value when it is exposed to a hydrogen gas but the current value drops to zero (0) when the hydrogen gas is removed.

The foregoing descriptions of specific exemplary embodiments of the present invention have been presented for the purposes of illustration and description. They are not intended to be exhaustive or to limit the invention to the precise forms disclosed, and obviously many modifications and variations are possible in light of the above teachings. It is intended that the scope of the invention be defined by the Claims appended hereto and their equivalents.

The invention claimed is:

1. A method of manufacturing a hydrogen sensor comprising the steps of:
    forming a thin film made of a transition metal or an alloy thereof on a surface of an elastic substrate, and
    forming a plurality of nanogaps in the thin film formed on the surface of the elastic substrate by applying a tensile force to the elastic substrate,
    wherein the nanogaps are formed as the thin film is stretched in a direction in which the tensile force acts while being contracted in a direction perpendicular to the direction in which the tensile force acts when the tensile force is applied, and is contracted again in the direction in which the tensile force is released while being stretched again in the direction perpendicular to the direction in which the tensile force is released when the tensile force is released.

2. The method according to claim 1, wherein the transition metal is selected from among Pd, Pt, Ni, Ag, Ti, Fe, Zn, Co, Mn, Au, W, In, and Al.

3. The method according to claim 1, wherein the alloy is selected from among Pd—Ni, Pt—Pd, Pd—Ag, Pd—Ti, Pd—Fe, Pd—Zn, Pd—Co, Pd—Mn, Pd—Au, Pd—W, Pt—Ni, Pt—Ag, Pt—Ag, Pt—Ti, Fe—Pt, Pt—Zn, Pt—Co, Pt—Mn, Pt—Au, and Pt—W.

4. The method according to claim 1, wherein the transition metal is Pd and the alloy is a Pd alloy.

5. The method according to claim 1, wherein the thin film formed on the surface of the elastic substrate is made of a $Pd_xNi_{1-x}$ alloy that satisfies the relationship: $0.85<x<0.96$.

6. The method according to claim 5 wherein the thin film formed on the surface of the elastic substrate is made of a $Pd_xNi_{1-x}$ alloy that satisfies the relationship: $0.90<x<0.94$.

7. The method according to claim 1, wherein the elastic substrate is a substrate that has a Poisson's ratio ranging from 0.2 to 0.8.

8. The method according to claim 1, wherein the tensile force is applied so that the elastic substrate is stretched 1.05 to 1.50 times.

9. The method according to claim 1, wherein the elastic substrate is made of natural rubber, synthetic rubber, or polymer.

10. The method according to claim 1, wherein the tensile force is applied repeatedly one or more times to the elastic substrate.

11. The method according to claim 1, wherein the tensile force is applied to the elastic substrate in one or more directions.

12. The method according to claim 11, wherein the tensile force is applied repeatedly in a first direction, a second direction perpendicular to the first direction, and a third direction different from the first and second directions.

13. The method according to claim 1, wherein the thin film has a thickness ranging from about 1 nm to about 100 μm.

14. The method according to claim 1, wherein the nanogaps are formed with a spacing ranging from about 1 nm to about 10 μm.

15. The method according to claim 1, further comprising the step of heat treating the thin film made of a transition metal or an alloy thereof in which the nanogaps are formed.

16. The method according to claim 1, further comprising the step of performing ion milling on the thin film made of a transition metal or an alloy thereof in which the nanogaps are formed.

17. A method of manufacturing a hydrogen sensor comprising the steps of:
preparing an elastic substrate; forming a thin film made of Pd or a Pd alloy on the elastic substrate, the Pd or Pd alloy having α phase;
forming nanogaps in the thin film in response to volume expansion by changing the α phase of the thin film into β phase by exposing the thin film to hydrogen-containing gas having a predetermined concentration of hydrogen; and
changing the β phase of the thin film into the α phase again by stopping the exposure of the thin film to the hydrogen-containing gas.

18. The method according to claim 17, further comprising the step of heat treating the thin film, in which the β is changed into the α phase.

19. The method according to claim 17, further comprising the step of performing ion milling on the thin film, in which the β is changed into the α phase.

20. The method according to claim 17, wherein when exposing the thin film to hydrogen-containing gas having a predetermined concentration, the concentration of hydrogen ranges from 2% to 15%.

21. The method according to claim 17, wherein the thin film has a thickness ranging, approximately, from 1 nm to 100 μm.

22. A hydrogen sensor comprising:
a substrate made of an elastic material;
a thin film formed on a surface of the substrate, the thin film being made of a transition metal or an alloy thereof; and
electrodes formed at opposite ends of the thin film,
wherein the thin film has a plurality of nanogaps formed therein by a tensile force that is applied to the substrate.

23. The hydrogen sensor according to claim 22, wherein the transition metal is selected from among Pd, Pt, Ni, Ag, Ti, Fe, Zn, Co, Mn, Au, W, In, and Al.

24. The hydrogen sensor according to claim 22, wherein the alloy is selected from among Pd—Ni, Pt—Pd, Pd—Ag, Pd—Ti, Pd—Fe, Pd—Zn, Pd—Co, Pd—Mn, Pd—Au, Pd—W, Pt—Ni, Pt—Ag, Pt—Ag, Pt—Ti, Fe—Pt, Pt—Zn, Pt—Co, Pt—Mn, Pt—Au, and Pt—W.

25. The hydrogen sensor according to claim 24, wherein the thin film is made of a $Pd_xNi_{1-x}$ alloy that satisfies the relationship: $0.85<x<0.96$.

26. The hydrogen sensor according to claim 25, wherein the thin film is made of a $Pd_xNi_{1-x}$ alloy that satisfies the relationship: $0.90<x<0.94$.

27. The hydrogen sensor according to claim 22, wherein the thin film has a thickness ranging from about 1 nm to about 100 μm.

28. The hydrogen sensor according to claim 22, wherein the nanogaps are formed with a spacing ranging from about 1 nm to about 10 μm.

29. A hydrogen sensor comprising:
a substrate made of an elastic material;
a thin film formed on a surface of the substrate, the thin film being made of Pd or a Pd alloy; and
electrodes formed at opposite ends of the thin film,
wherein the thin film has a plurality of nanogaps formed according to a method of manufacturing a hydrogen sensor comprising the steps of: forming the thin film made of Pd or a Pd alloy on the elastic substrate, the Pd or Pd alloy having a phase; forming nanogaps in the thin film in response to volume expansion by changing the α phase of the thin film into β phase by exposing the thin film to hydrogen-containing gas having a predetermined concentration of hydrogen; and changing the β phase of the thin film into the α phase again by stopping the exposure of the thin film to the hydrogen-containing gas.

* * * * *